United States Patent
Grotendorst (12)

(10) Patent No.: US 6,464,983 B1
(45) Date of Patent: Oct. 15, 2002

(54) METHODS AND USES OF CONNECTIVE TISSUE GROWTH FACTOR FOR DIFFERENTIATION OF MESENCHYMAL STEM CELLS

(75) Inventor: Gary R. Grotendorst, Miami, FL (US)

(73) Assignees: University of South Florida, Tampa, FL (US); University of Miami, Miami, FL (US)

(*) Notice: Subject to any disclaimer, the term of this patent is extended or adjusted under 35 U.S.C. 154(b) by 0 days.

(21) Appl. No.: 09/122,135

(22) Filed: Jul. 24, 1998

Related U.S. Application Data

(63) Continuation of application No. 08/656,393, filed on May 31, 1996, now Pat. No. 5,837,258, which is a continuation-in-part of application No. 08/459,717, filed on Jun. 2, 1995, now Pat. No. 5,770,209, which is a continuation-in-part of application No. 08/386,680, filed on Feb. 10, 1995, now Pat. No. 5,585,270, which is a division of application No. 08/167,628, filed on Dec. 14, 1993, now Pat. No. 5,408,040, which is a continuation-in-part of application No. 07/752,427, filed on Aug. 30, 1991, now abandoned.

(51) Int. Cl.$^7$ .............................................. A61K 38/18
(52) U.S. Cl. ........................ 424/198.1; 514/43; 530/399
(58) Field of Search ...................... 424/198.1; 435/69.1; 536/23.5; 530/399; 514/43

(56) References Cited

U.S. PATENT DOCUMENTS

| | | |
|---|---|---|
| 5,149,691 A | 9/1992 | Rutherford |
| 5,356,630 A | 10/1994 | Laurencin et al. |
| 5,399,361 A | 3/1995 | Song et al. |
| 5,408,040 A | 4/1995 | Grotendorst et al. |

OTHER PUBLICATIONS

Shimokado et al., Cell 43:277–286, Nov. 1985.
Campochiaro et al., Exp. Eye Res. 49:217–227, 1989.
Matsuoka et al., Proc. Nat. Acad. Sci. 86:4416–4420, Jun. 1989.

Ryseck et al., Cell Growth and Differentiation, 2:225–233, May 1991.

P. Cassiede et al., "Osteochondrogenic potential of marrow mesenchymal progenitor cells exposed to TGF–β1 or PDG-F–BB as assayed in vivo and in vitro", Journal of Bone and Mineral Research 11(9):1264–1273, 1996.*

E.A. Wang et al., "Bone morphogenic protein–2 causes commitment and idfferentiation in C3H10T1/2 and 3T3 cells", Growth Factors 9:57–71, 1993.*

A.H. Reddi et al., "Bone induction by osteogenin and bone morphogenic proteins", Biomaterials 11:33–34, 1990.*

Bradham et al., "Connective Tissue Growth Factor: a Cysteine–rich Mitogen Secreted by Human Vascular Endothelial Cells Is Related to the SRC–induced Immediate Early Gene Product CEF–10," *The Journal of Cell Biology* 114(6):1285–1294 (1991).

Igarashi et al., "Regulation of Connective Tissue Growth Factor Gene Expression in Human Skin Fibroblasts and During Wound Repair," *Molecular Biology of the Cell* 4:637–645 (1993).

Kimura, Yusuke. "Expression of a connective tissue growth factor (CTGF) gene in a human chondrosarcoma–derived chondrocytic cell line and analysis of its function," *Osaka Daigaku Shigaku Zasshi* (1996) and *Chemical Abstracts*, abstract No. 239360 125(19):253 Columbus, Ohio, US (1996).

* cited by examiner

*Primary Examiner*—Lorraine Spector
(74) *Attorney, Agent, or Firm*—Gray Cary Ware & Freidenrich, LLP; Lisa A. Haile; Richard J. Imbra

(57) ABSTRACT

The present invention relates to novel methods and compositions related to the administration of connective tissue growth factor, alone or in combination with other growth factors, compositions or compounds, to induce the differentiation of mesenchymal stem cells into chondrocytes or asteablasts.

4 Claims, 15 Drawing Sheets

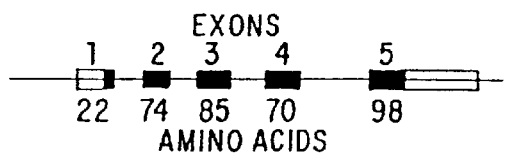

FIG. 1A

```
-823 CTGF
TCTAGAGCTCGCGCGAGCTCTAATACGACTCACTATAGGGCGTCGACTCGATCCCTTTT- CTGF
 ***   **  *  *    ** ** * *    ***   *  *** **       **  ***
TCT—TTCT-TCTCCCACTATATTCCCTGACAC—TTAGGCTTCTGAAGATAGCCATTTG FISP

-TCTGGAAACATTGA-TGGCCACTCGTCCCTTGTCCTTGCCTATATAAAACTCCTACATA CTGF
 ****  *  *** * *     **       ** ****  *   *  *  *  * *
GTCTGAACTCATAAACTTATTTTTCTA—GAAAACCATGCCCAGTAATACCCCTTGCCTG FISP

-706 CTGF
TATTAAG—AGAAAACTAA———GCA———AGAGTTTTGGAAATCTGCCCCAGGAGACTG CTGF
 *  *   *** ** *        **   *****  ** ******  **  ***   **
CCTTGACCCTGAAGACAAGTTCTTACATAAAGAGTGCTGAAAATCTT-CCTGGGAACCTA FISP
         AP-1
CATCC|TGAGTCA|CACGAGTCTTTGTTCTCTTTCTTGTCCCAAAACCGTTACCTCAAGTGA CTGF
 ******   *  *     ****  *  * **      *   ** *    *** *****
CATCCT-TGGCTTTCATATCTTTCAGC-C-ATCAAA———ATGCCAT——CTCCAGTGA FISP

-596 CTGF
-CAAATGATCAAATCTCAAATATAGAATTCAGG-GTTTTACA—GGTAGGCATCTTGAGG CTGF
 **** ******  *   ** *   ** **   ***  ***  **  *   *     *  *
CCAAA-GATCAATGCCTGTATTTCAGATACAAAAGTTGCACATAGGAATTCTGGGAGGAG FISP

ATTTCAAATGGTTAAAAGCAACT-CACTCCTTTTCTACTCT-TTGGAGAGTTTCAAGAG CTGF
  *    **  ** ** *  ***  **** **  ***  *  * ***        ******
AGGAGGCATTTCAAATGGCTATAAGCAC-CCTTCTCCTCTCAGTAGAAGAACACCAAGAG FISP

-483 CTGF
CCTATAGCCTCT————AAAACGCAAATCATTGCTAAGGGTTGGGGGGGAGAAACCTTTT CTGF
 *** ****  *         ****    *** *  *  ***      *    **   ****
ACTACAGCCCCGTAAAGAAAAAAAAAAAAAAAATCCAAAACAAAGAAAAAGAAATATTTT FISP
                                            CArGbox
CGAATTTTTTAGGAATTCCTGCTGTTTGCCTCTTCAGCTACCTACTT|CCTAAAAAGG|ATG CTGF
  * *** ****   *  ** * ********** *****   *     **  *  ***   *
TTTAATTTCTAGGGGCCCATGGTATTTGCCTCTTGAGCTATTTGAGTCTTGAGAAGTTTT FISP
                                                 AP-1
-368 CTGF
TATGTCAGTGGACAGAACAGGGCAAACTTATTCGAAAAAGAAATAA—GAAATAATTGCC CTGF
 ********  * ****** ** **  ** ** ****** *  *  *     *  ***  *
TATGTCAGTAGCCAGAACTGGCAAAGAGATTTTTAAGAAGAAAAGATCAGAGAAATAATC FISP
                    AP-1
AGTGTGTTTATAAATGATA|TGAATCA|GGAGTGGTGCGAAGAGGATA-GGAAAAAAAAATT CTGF
 *   ** * * *       *   ********  ****  **** ****  *** ***       *
GTTTATTTCTAAGTTATATTTCATCAGGAGGGGTGAGAAGACGATATGGAGAAAGTTTTA FISP
```

FIG. 1B1

```
-251 CTGF
CTATTTGGTGCTGGAAATACTGCGCTTTTTTTTTCCTTTTTTTTTTTTT—CTGT-GAGC CTGF
 **  *****  **           * *            **************  ***  ****
CTATTTGGTGTTGTGCTGGAAACAC———AGCGCCTTTTTTTTTTTTTTCCTGGCGAGC FISP
    NF-1-LIKE                        TGF-β ELEMENT
TGGAGTGTGCCAGCTTTTTCAGACGGAGGAATGCTGAGTGTCAAGGGGTCAGGATCAATC CTGF
 *  ******************************* ***************** **********
TAAAGTGTGCCAGCTTTTTCAGACGGAGGAATGTGGAGTGTCAAGGGGTCAGGATCAATC FISP

-134 CTGF
     TIE-LIKE
CGGTGTGAGTTGATGAGGCAGGAAGGTGGGGAGGAATGCGAGGAATGTCCCTGTTTGTGT CTGF
***** ************** ************************ ********************
CGGTGTGAGTTGATGAGGCAGGAAGGTGGGGAGGAATGTGAGGAATGTCCCTGTTTGTGT FISP
            CATbox           SP-1        TATAbox
AGGACTCCATTCAGCTCATTGGCGAGCCGCGGCCGCCCGGAGCGTATAAAAGCCTCGGG CTGF
******  ******  ** ********   **  ** ************* ***   *  *
AGGACTTCATTCAGTTCTTTGGCGAGCCG—GCTCCCGGGAGCGTATAAAAGCCA-GCC FISP -15 CTGF
    SP-1        +1
CCGCCCGCCCCAAACTCACACAACAACTCTTC CTGF
******  ***   * *******     *****
CCGCCCGCCCT-AGTCTCACACAG——CTCTTC FISP
```

FIG.1B2

-823 TCTAGAGCTCGCGCGAGCTCTAATACGACTCACTATAGGGCGTCGACTCGATCCCTTTTT

-763 CTGGAAACATTGATGGCCACTCGTCCCTTGTCCTTGCCTATATAAAACTCCTACATATAT

-703 TAAGAGAAAACTAAGCAAGAGTTTTGGAAATCTGCCCCAGGAGACTGCATCC<u>TGAGTCAC</u>
                                                                   AP-1

-643 ACGAGTCTTTGTTCTCTTTCTTGTCCCAAAACCGTTACCTCAAGTGACAAATGATCAAAT

-583 CTCAAATATAGAATTCAGGGTTTTACAGGTAGGCATCTTGAGGATTTCAAATGGTTAAAA

-523 GCAACTCACTCCTTTTCTACTCTTTGGAGAGTTTCAAGAGCCTATAGCCTCTAAAACGCA

-463 AATCATTGCTAAGGGTTGGGGGGGAGAAACCTTTTCGAATTTTTTAGGAATTCCTGCTGT

-403 TTGCCTCTTCAGCTACCTACTT<u>CCTAAAAAGG</u>ATGTATGTCAGTGGACAGAACAGGGCAA
                               CArG box -343 ACTTATTCGAAAAAGAAATAAGAAATAATTGCCAGTGTGTTTATAAATGATA<u>TGAATCAG</u>
                                                           AP-1

-283 GAGTGGTGCGAAGAGGATAGGAAAAAAAAATTCTATTTGGTGCTGGAAATACTGCGCTTT

-223 TTTTTTCCTTTTTTTTTTTTTCTGTGAGC<u>TGGAGTGTGCCAG</u>CTTTTTCAGACGGAGGAA
                                    NF-1 LIKE

-163 TGCTGAGTGTCAAGGGGTCAGGATCAATCCGGTGTG<u>AGTTGATG</u>AGGCAGGAAGGTGGGG
                                                   TIE-LIKE

-103 AGGAATGCGAGGAATGTCCCTGTTTGTGTAGGACTCCATTCAGCTC<u>ATTGG</u>CGAGCCGCG
                                                               CATbox -43 G<u>CCGCCC</u>GGAGCG<u>TATAAAAG</u>CCTCGGG<u>CCGCCCGCCCC</u>AAACTCACACAACAACTCTTC
        SP-1       TATAbox       SP-1       +1

17 CCCGCTGAGAGGAGACAGCCAGTGCGACTCCACCCTCCAGCTCGACGGCAGCCGCCCCGG

77 CCGACAGCCCCGAGACGACAGCCCGGCGCGTCCCGGTCCCCACCTCCGACCACCGCCAGC

137 GCTCCAGGCCCCGCGCTCCCCGCTCGCCGCCACCGCGCCCTCCGCTCCGCCCGCAGTGCC

197 AACCATGACCGCCGCCAGTATGGGCCCCGTCCGCGTCGCCTTCGTGGTCCTCCTCGCCCT
        M  T  A  A  S  M  G  P  V  R  V  A  F  V  V  L  L  A
 257 CTGCAGCCGGGTAAGCGCCGGGAGCCCCCGCTGCGGCCGGCGGCTGCCAGGGAGGGACTC
     L  C  S  R  ..........INTRON 1.....................
 317 GGGGCCGGCCGGGGAGGGCGTGCGCGCCGACCGAGCGCCGCTGACCGCCCTGTCCTCCCT
 377 GCAGCCGGCCGTCGGCCAGAACTGCAGCGGGCCGTGCCGGTGCCCGGACGAGCCGGCGCC
    ....P  A  V  G  Q  N  C  S  G  P  C  R  C  P  D  E  P  A
 437 GCGCTGCCCGGCGGGCGTGAGCCTCGTGCTGGACGGCTGCGGCTGCTGCCGCGTCTGCGC
     P  R  C  P  A  G  V  S  L  V  L  D  G  C  G  C  C  R  V  C

FIG. 1C1

```
 497 CAAGCAGCTGGGCGAGCTGTGCACCGAGCGCGACCCCTGCGACCCGCACAAGGGCCTCTT
      A K Q L G E L C T E R D P C D P H K G L
 557 CTGTGACTTCGGCTCCCCGGCCAACCGCAAGATCGGCGTGTGCACCGGTAAGACCCGCAG
      F C D F G S P A N R K I G V C T  ...INTRON 2..
 617 CCCCCACCGCTAGGTGTCCGGCCGCCTCCTCCCTCACGCCCACCCGCCCGCTGGAAAAAG
 677 AAACCGCTCGGACTGAGTTTCTTTCTCCAGCTGCTGCCAGCCCGCCCCCTGCAGCCCAGA
 737 TCCCAACTCGCATCCCTGACGCTCTGGATGTGAGAGTGCCCCAATGCCTGACCTCTGCAT
 797 CCCCCACCCCTCTCTTCCCTTCCTCTTCTCCAGCCAAAGATGGTGCTCCCTGCATCTTCG
      .................................A K D G A P C I F
 857 GTGGTACGGTGTACCGCAGCGGAGAGTCCTTCCAGAGCAGCTGCAAGTACCAGTGCACGT
      G G T V Y R S G E S F Q S S C K Y Q C T
 917 GCCTGGACGGGGCGGTGGGCTGCATGCCCCTGTGCAGCATGGACGTTCGTCTGCCCAGCC
      C L D G A V G C M P L C S M D V R L P S
 977 CTGACTGCCCCTTCCCGAGGAGGGTCAAGCTGCCCGGGAAATGCTGCGAGGAGTGGGTGT
      P D C P F P R R V K L P G K C C E E W V
1037 GTGACGAGCCCAAGGACCAAACCGTGGTTGGGCCTGCCCTCGCGGGTGAGTCGAGTCTTC
      C D E P K D Q T V V G P A L A .................
1097 CTCTAAGTCAGGGTCGTGATTCTCTCCCAGGGAGGGAGTCCTAACTGTGCCGACCGAACG
1157 GGGAAATACCTTATCAGGCGTTTTACATGGTGTTTGTGTGCTCTGCTCTCGCAGCTTACC
      ...........INTRON 3...................................A Y
1217 GACTGGAAGACACGTTTGGCCCAGACCCCAACTATGATTAGAGCCAACTGCCTGGTCCAGA
      R L E D T F G P D P T M I R A N C L V Q
1277 CCACAGAGTGGAGCGCCTGTTCCAAGACCTGTGGGATGGGCATCTCCACCCGGGTTACCA
      T T E W S A C S K T C G M G I S T R V T
1337 ATGACAACGCCTCCTGCAGGCTAGAGAAGCAGAGCCGCCTGTGCATGGTCAGGCCTTGCG
      N D N A S C R L E K Q S R L C M V R P C
1397 AAGCTGACCTGGAAGAGAACATTAAGGTACATGTTCTGCTCCTATTAACTATTTTTCACA
      E A D L E E N I K............INTRON 4............
1457 GGAAAAACAGTGGATAGGACCCAACTTAGGGCTCTTGCACGCTTGTTAGTATAAGCCCGT
1517 TATCTCCAAAACTATCTAACCATTGAGCTGTTTTGCTGGAATGAGAGCTTGTGTAATAGC
1577 AACCACCAGTTTTCCACTACGAAATCTTCCACAGGGTTAGTTAATTCAAGACATTCCAAG
1637 AGAGGCTCTGGCTATTTTTGGACATAGCAAATGAGACTCAAACTTCCTCCCCTCAAAATA
1697 TAAACAGAAGTCAGACAACAGAAGACTAAAACACAGAGGGTTGAAGAAAGCCACTCCTCT
1757 TGTAGAGTCGCTGATTTTTTTTTTTCCTCTCTCTTTTCCCTTGTCTTCCTTAGAAGGGCA
      ...........................................................K G
1817 AAAAGTGCATCCGTACTCCCAAAATCTCCAAGCCTATCAAGTTTGAGCTTTCTGGCTGCA
      K K C I R T P K I S K P I K F E L S G C
1877 CCAGCATGAAGACATACCGAGCTAAATTCTGTGGAGTATGTACCGACGGCCGATGCTGCA
      T S M K T Y R A K F C G V C T D G R C C
1937 CCCCCCACAGAACCACCACCCTGCCGGTGGAGTTCAAGTGCCCTGACGGCGAGGTCATGA
      T P H R T T T L P V E F K C P D G E V M
1997 AGAAGAACATGATGTTCATCAAGACCTGTGCCTGCCATTACAACTGTCCCGGAGACAATG
      K K N M M F I K T C A C H Y N C P G D N
```

FIG. 1C2

```
2057 ACATCTTTGAATCGCTGTACTACAGGAAGATGTACGGAGACATGGCATGAAGCCAGAGAG
      D   I   F   E   S   L   Y   Y   R   K   M   Y   G   D   M   A   *
2117 TGAGAGACATTAACTCATTAGACTGGAACTTGAACTGATTCACATCTCATTTTTCCGTAA
2177 AAATGATTTCAGTAGCACAAGTTATTTAAATCTGTTTTTCTAACTGGGGGAAAAGATTCC
2237 CACCCAATTCAAAACATTGTGCCATGTCAAACAAATAGTCTATCTTCCCCAGACACTGGT
2297 TTGAAGAATGTTAAGACTTGACAGTGGAACTACATTAGTACACAGCACCAGAATGTATAT
2357 TAAGGTGTGGCTTTAGGAGCAGTGGGAGGGTACCGGCCCGGTTAGTATCATCAGATCGAC
2417 TCTTATACGAGTAATATGCCTGCTATTTGAAGTGTAATTGAGAAGGAAAATTTTAGCGTG
2477 CTCACTGACCTGCCTGTAGCCCCAGTGACAGCTAGGATGTGCATTCTCCAGCCATCAAGA
2537 GACTGAGTCAAGTTGTTCCTTAAGTCAGAACAGCAGACTCAGCTCTGACATTCTGATTCG
2597 AATGACACTGTTCAGGAATCGGAATCCTGTCGATTAGACTGGACAGCTTGTGGCAAGTGA
2657 ATTTGCCTGTAACAAGCCAGATTTTTTAAAATTTATATTGTAAATATTGTGTGTGTGTGT
2717 GTGTGTGTATATATATATATATATGTACAGTTATCTAAGTTAATTTAAAGTTGTTTGTGC
2777 CTTTTTATTTTTGTTTTTAATGCTTTGATATTTCAATGTTAGCCTCAATTTCTGAACACC
2837 ATAGGTAGAATGTAAAGCTTGTCTGATCGTTGAAAGCATGAAATGGATACTTATATGGAA
2897 ATTCTGCTCAGATAGAATGACAGTCCGTCAAAACAGATTGTTTGCAAAGGGGAGGCATCA
2957 GTGTCTTGGCAGGCTGATTTCTAGGTAGGAAATGTGGTAGCTCACGTTTAATGAACAAAT
3017 GGCCTTATTAAAAACTGAGTGACTCTATATAGCTGATCAGTTTTTCACCTGAAGCATTTG
3077 TTTCTACTTTGATATGACTGTTTTTCGACAGTTTATTTGTTGAGAGTGTGACCAAAAGTT
3137 ACATGTTTGCACCTTTCTAGTTGAAAATAAAGTGTATATTTTTCTATAAAGGGCTTGGT
3197 TATTCATTTATCCTTCTAAACATTTCTGAGTTTTCTTGAGCATAAATAGGAAGTTCTTAT
3257 TAATCATAAGATAATTCACCAATAATTTTCTAAATATCTTTAATTATTCTATACATTAAT
3317 AAATTGATTATTCCATAGAATTTTTATGTAAACATACTTCACACTGAATCAAGTATCACA
3377 GACTTGCAGGCATA
```

FIG. 1C3

METHODS AND USES OF CONNECTIVE TISSUE GROWTH FACTOR FOR DIFFERENTIATION OF MESENCHYMAL STEM CELLS

1. STATEMENT OF RELATED CASES

This is a continuation of U.S. application Ser. No. 08/656,393, filed May 31, 1996, issued as U.S. Pat. No. 5,837,258, which is a CIP of Ser. No. 08/459,717 filed Jun. 2, 1995 now U.S. Pat. No. 5,870,209 which is a CIP of Ser. No. 08/386,680, filed Feb. 10, 1995, now U.S. Pat. No. 5,585,270, which is a divisional of U.S. patent application Ser. No. 08/167,628, filed Dec. 14, 1993, which is now U.S. Pat. No. 5,408,040, which is a file-wrapper continuation of U.S. patent application Ser. No. 07/752,427, filed Aug. 30, 1991 now abandoned.

The information disclosed in this Specification was made in part with Government support by grant no. GM 37223, awarded by the National Institute of Health. The government may have certain rights in the invention disclosed in this Specification.

2. FIELD OF THE INVENTION

This invention relates generally to the field of growth factors and specifically to Connective Tissue Growth Factor (CTGF) and methods of use thereof.

3. BACKGROUND OF THE INVENTION

A. The Role Of Growth Factors in Bone and Cartilage Formation

Bone And Cartilage Formation. The formation of tissue and organs in all multicellular organisms that arise from a single fertilized egg requires the differentiation of specialized cell types from non-differentiated stem cells. As embryogenesis proceeds, more highly specialized cell types and complex structures are formed. Currently, however, little concrete information is available on the identification of the specific factors or the mechanism of action of these factors on skeletal or cartilage formation in vertebrate animals, including humans.

There are two common types of bone formation in the mammalian system: intramembranous ossification and ehdochondral ossification. The formation of the bones of the skull are an example of intramembranous ossification. There, mesenchymal cells from the neural crest interact with the extracellular matrix of the cranial epithelial cells and form bone. Hall, *Amer. Sci.*, 1988, 76174–181. Mesenchymal cells condense into small islands and differentiate into osteoblasts and capillaries. The osteoblasts secrete a specific type of extracellular matrix, (osteoid) which is capable of binding calcium salts.

Endochondral ossification is the process by which the long bones of the axial skeleton (arms and legs), and the vertebra and ribs form. Hall, supra. During this process the formation of bone occurs via a cartilaginous tissue intermediate stage. In mammals, the long bones form from certain mesenchymal cells in the embryonic limb buds. These cells form chondrocytes, and secrete a cartilaginous matrix. Other surrounding mesenchymal cells form the perichondrium (ultimately, the periosteum). In some cases, chondrocytes adjacent to the region where chondrocytes are proliferating and forming differentiate into hypertrophic chondrocytes.

Hypertrophic chondrocytes produce a different type of matrix, and alter their tissue orientation to form the physis. The structure of the physis is arranged in multiple 30 cellular columns composed of zones of cellular hypertrophy, proliferation, ossification and vascularization. Hall, supra; Gilbert, "Transcriptional regulation of gene expression," DEVELOPMENTAL BIOLOGY, 5th ed. Sinaur Assoc., p. 387–390 (1994). This results in a gradation of cell transformation from chondrocytes to osteoblasts which form the mineralized-bone.

Endochondral ossification is an active, ongoing process that occurs in mammals during the growth from infant to adult. The differentiation of mesenchymal cells to chondrocytes, their proliferation and replacement by osteoblasts are dependent on growth factors (including the TGF-$\beta$ family), and on the mineralization of the matrix. Tuan, 1984, *J. Exp. Zool.* (suppl.) 1:1–13 (1984); Syfestad and Caplan, 1984, *Devel. Biol.* 104:348–386.

With regard to connective tissue, it is felt that all skeletal elements in mammals are derived from a single stem cell that is capable of differentiating into the specific cell types that compose muscle, cartilage, bone and tendon. These cells also appear to be capable of differentiating into adipose tissue.

The Relevant Art Related To Growth Factors And The Formation Of Bone And Cartilage. Prior to the present invention, it was known generally that growth factors comprise a class of secreted polypeptides that stimulate target cells to proliferate, differentiate and organize developing tissues. Typically, a growth factor's activity is dependent on its ability to bind to specific receptors, thereby stimulating a signaling event within the cell. Examples of some well-studied growth factors include platelet-derived growth factor (PDGF), insulin-like growth factor (IGF-I), transforming growth factor beta family (TGF-$\beta$), transforming growth factor alpha (TGF-$\alpha$), epidermal growth factor (EGF), and fibroblast growth factors (FGF).

Effect Of TGF-$\beta$ On Chondrocyte Growth, Differentiation and Cartilage Formation. The TGF-$\beta$s play a role in chondrogenesis. As previously reported, TGF-$\beta$1 and TGF-$\beta$2 increase chondrogenesis in embryonic rat mesenchymal cells (Seyedin,et al.., 1987, *J. Biol. Chem.* 262: 1946–1947), and either isoform can induce formation of chondroblasts from murine muscle mesenchymal cells in culture. Seyedin. et al., 1986, *J. Biol. Chem.* 261: 5693–5695. Application of the TGF-$\beta$s to murine embryonic prechondroid tissues increases differentiation of mesenchymal cells, production of proteoglycans, and replication of chondroblasts. Centrella, et al., 1994, *Endocrine Reviews* 15:27–38; Thorp and Jakowlew, 1994, *Bone* 15: 59–64.

Using in-situ hybridization, decreased levels of TGF-$\beta$3 were found in the growth plates of animals with three separate disorders where chondrocytes cease to differentiate. Id. In organ cultures of bovine articular cartilage, type II collagen and proteoglycan synthesis were increased after TGF-$\beta$ administration. Morales and Roberts, 1988, *J. Biol. Chem.* 263: 12828–12831. In contrast, the TGF-$\beta$s have been shown to decrease expression of type II and type X cartilage-specific collagens, synthesis of chondrocyte proteoglycans, and activity of alkaline phosphatase in cultured chondroid cells. Mundy. "The effects of TGF-$\beta$ on bone," *Clinical Applications of TGF-$\beta$.*, 1991, Wiley Chichester, Ciba Foundation Symposium 157: 137–151. Rabbit growth plate chondrocyte differentiation is inhibited by TGF-$\beta$, while growth plate chondrocyte mitogenesis is increased. Kato, et al., 1988, *Proc. Natl. Acad. Sci. USA* 85: 9552–9556. In addition, large concentrations of TGF-$\beta$1 or TGF-$\beta$2 added to an osteoinductive model favor cartilage, rather than the preference for bone formation, when smaller doses are used. Mundy, supra. This accumulation of apparently contradictory data has hindered efforts to define a function for the TGF-$\beta$s in chondrogenesis.

The Bone Morphogenic Proteins And Bone Formation. A family of proteins termed the bone morphogenetic proteins (BMP's are capable of inducing ectopic bone formation in certain mammalian species. With the exception of BMP-1, which encodes a metalloprotease, all of these proteins have structures that are related to TGF-β. However, it is not known which, if any of the BMP's are responsible for the regulation of bone formation during normal embryogenesis.

BMP's were first isolated from demineralized bone as factors that induced bone at extra skeletal ectopic sites. Three peptides were originally identified as BMP-1, BMP-2A, and BMP-3. Celeste, et al., 1990, *Proc. Natl Acad. Sci. USA* 87: 984.3–9847; Kubler and Urist, 1990, *Clin. Orthopedics and Rel. Res.* 258: 279–294. The latter two BMPs are members of the TGF-β superfamily. Subsequently, five more closely related members of the BMP group have been identified and cloned. BMP-5, BMP-6, and BMP-7 are most similar to vgr/60A, while BMP-2 and BMP-4 are more similar to Decapentaplegic. Both vga/60A and Decapentaplegic are Drosophila genes that control dorsal/ventral axis pattern formation. Hoffman, 1992, *Mol. Repro and Dev.* 32: 173–178.

In-situ hybridization has localized BMP's gene transcription to areas of bone formation in the limb bud at specific times during development, suggesting a physiologic role. The BMPs induce adventitial post-fetal mesenchymal cells to switch from fibrogenetic to chondroosteoprogenetic patterning. Kubler and Urist, supra. Several lines of data suggest the BMPs may act synergistically with TGF-βs to initiate the cascade of osteoinduction in-vivo. In murine subcutis, TGF-β1 enhances the production of ectopic bone by most BMPs. BMP-6 (also known as VGR-1) is expressed in hypertrophic cartilage at the same time and in the same areas as the TGF-βs, and is associated with collagen type X expression. See, Celeste, et al., supra.

The addition of TGFβ-2 to bone explants which have been treated with either BMP-2 or BMP-3 results in increased osteoinductive activity and an increased ratio of cartilage to bone when compared to either factor alone. Bentz, et al., 1991, *Matrix* 11:269–275. However, the synergistic effect of these proteins by the TGF-βs is not universal. TGF-β1 has been shown to directly decrease BMP-2 expression in fetal rat calvaria cultures. Harris, et al., 1994, *J. Bone and Mineral Res.* 9: 855–863. Since BMP-2 is apparently important in bone cell differentiation, it has been suggested that TGF-β1 may be acting as a switch to monitor the differentiation fates of chondro- or osteo-blastic precursors.

Other Factors Found To Be Expressed In Developing Tissue. Cyr61 is a growth regulator which has been found to be expressed in developing mouse embryo and extraembryonic tissues. O'Brien and Lau, 1992, *Cell Growth Differ.* 3:645–654. Cyr61 is related to but distinct from CTGF and prior to the instant invention, the specific activity of Cyr61 was not known.

B. The Role of Growth Factors in Wound Healing Platelet Derived Growth Factor and Wound Healing.

PDGF is a dimeric molecule consisting of an A chain and a B chain. The chains form heterodimers of homodimers and all combinations isolated to date are biologically active. With respect to the factor's activity, PDGF has been characterized as a cationic, heat-stable protein found in the α-granules of circulating platelets. The molecule has been further characterized as a mitogen and a chemotactic agent for connective tissue cells such as fibroblasts and smooth muscle cells.

Because of PDGF's biological activity and release during wound healing, PDGF has been identified as a growth factor involved in wound healing, as well as pathological conditions showing on overproduction of connective tissue, including atherosclerosis and fibrotic diseases.

It has been hypothesized that growth factors other than PDGF may play a role in the normal development, growth, and repair of human tissue.

TGF-β And Wound Healing. The formation of new and regenerating tissue requires the coordinate regulation of various genes that produce both regulatory and structural molecules which participate in the process of cell growth and tissue organization. As with bone induction, it appears that TGF-β plays a central regulatory component of this process. TGF-β is released by platelets, macrophages and neutrophils which are present in the initial phases of the repair process. TGF-β can act as a growth stimulatory factor for mesenchymal cells and as a growth inhibitory factor for endothelial and epithelial cells. It has been suggested that the growth-stimulatory action of TGF-β appears to be mediated via an indirect mechanism involving the induction of other genes including growth factors such as PDGF.

Several members of the TGF-β superfamily possess activities suggesting possible applications for the treatment of cell proliferative disorders, such as cancer. In particular, TGF-β has been shown to be potent growth inhibitor for a variety of cell types (Massague, 1987, *Cell 49:437*), MIS has been shown to inhibit the growth of human endometrial carcinoma tumors in nude mice (Donahoe, et al., 1981, *Ann. Surg.* 194:472), and inhibition has been shown to suppress the development of tumors both in the ovary and in the testis (Matzuk, et al., 1992, *Nature*, 360:313).

Many of the members of the TGF-β family are also important mediators of tissue repair. TGF-β has been shown to have marked effects on the formation of collagen and causes of striking angiogenic response in the newborn mouse (Roberts, et al., 1986, *Proc. Natl. Acad. Sci., USA* 83:4167). The bone morphogenic proteins (BMPs) can induce new bone growth and are effective for the treatment of fractures and other skeletal defects (Glowacki, et al., 1981 Lancet, 1:959; Ferguson, et al., 1988, *Clin. Orthoped. Relat. Res.*, 227:265; Johnson, et al., 1988, *Clin. Orthoped. Relat. Res.*, 230:257).

C. Connective Tissue Growth Factor

A previously unknown growth factor, related to PDGF, and termed Connective Tissue Growth Factor (CTGF), has been reported in a related patent. See, U.S. Pat. No. 5,408, 040. CTGF is a cysteine-rich mitogenic peptide which is selectively induced in fibroblasts after activation with TGF-β. Igarashi, et al., 1993, *Mol. Biol. Cell* 4:637–645.

CTGF is a member of a family of peptides that include serum induced gene products ceflo (Simmons, et al., 1989, *Proc. Natl. Acad. Sci. USA* 86:1178–1182), cyr61 (O'Brien, et al., 1990, *Mol. Cell. Biol.* 10:3569–3577), fisp12/IG M1 (Ryseck, et al., 1993, *Cell Growth & Differ.* 2:225–233), and a chicken-transforming gene, nov (Joliot, et al. 1992, *Mol. Cell Biol.* 12:10–21 (1992). CTGF also shares sequence homology with a drosophila gene product, twisted gastrulation (twg) (Mason, et al.., 1994, *Genes & Develop.* 8:1489–1501), which determines cell fates during dorsal/ventral pattern formation in the embryo.

As reported in that patent, CTGF is the product of a distinct gene. As also reported in U.S. Pat. No. 5,408,040, CTGF possesses mitogenic activity. The ultimate result of this mitogenic activity in vivo, is the growth of targeted tissue. CTGF also possesses chemotactic activity, which is the chemically induced movement of cells as a result of interaction with particular molecules.

Although the molecule is antigenically related to PDGF, there is little if any peptide sequence homology between CTGF and PDGF. Anti-PDGF antibody has high affinity to the non-reduced forms of the PDGF isomers and the CTGF molecule and ten-fold less affinity to the reduced forms of these peptides, which lack biological activity.

A second protein, identified as "connective tissue growth factor-2" or "CTGF-2," has been reported also. See, PCT Application No. PCT/US94/07736 (International Publication No. WO 96/01896). According to the PCT Application, CTGF-2 may also be used to enhance the repair of connective and support tissue. Although identified as a connective tissue growth factor, CTGF-2 is not closely related to the CTGF of the present invention. Specifically, the CTGF family is comprised of three distinct groups of proteins: CTGF/Fisp12, cyr61 and nov. The protein of the claimed invention falls within the first group of proteins, as compared to CTGF-2, which falls with thecyr61 group. PCT Application No. PCT/US94/07736 at 4.

Notwithstanding the identification of various PDGF related growth factors, including CTGF, prior to the present invention, such factors have not been proven to be an effective induction agent for the production of matrices, including the induction of bone and/or cartilage tissue.

4. SUMMARY OF THE INVENTION

The subject invention provides novel methods and compositions for the treatment of diseases, disorders or ailments wherein matrix and/or connective tissue production, including the production of bone and/or cartilage, is desired. The subject invention is likewise directed to the treatment of diseases, disorders or ailments wherein the promotion of wound healing is desired.

More specifically, the compositions of the present invention comprise CTGF and/or fragments and/or derivatives thereof (hereinafter collectively "CTGF"), alone or in combination with other growth factors. The CTGF used in the subject compositions may be either obtained by isolation from natural sources, synthetic manufacture, or production by recombinant genetic engineering techniques.

In one aspect of the invention, the methods of the present invention comprise the administration of an effective amount of CTGF, alone or in combination with one or more compounds, to treat diseases, disorders or ailments wherein the induction of bone or cartilage tissue is desired. In a preferred embodiment of this method, such additional compound is a growth factor.

In another aspect of the invention, the methods of the present invention comprise the administration of an effective amount of CTGF, alone or in combination with one or more compounds, again preferably one or more growth factors, to treat diseases, disorders or ailments wherein the promotion of wound healing is desired.

In a preferred embodiment of the invention, the composition comprising CTGF is administered directly onto or into the site in which bone or cartilage induction is desired so as to induce the formation of such bone or cartilage. In another embodiment, the composition is formulated for targeted delivery or alternatively, are designed for the release of the novel compositions in the relevant site (e.g., the wound-in which cartilage formation is desired). In each case, the CTGF containing composition is appropriately formulated for administration to a patient in need.

5. DEFINITIONS

As used in this Specification, the term "CTGF" shall mean: (1) a protein encoded by the amino acid sequence set forth at FIG. 1C, (2) a protein having CTGF activity wherein such protein is encoded by the amino acid sequence of FIG. 1C wherein one or more amino acids have been added, deleted, mutated, substituted or otherwise altered ("derivative") and the nucleotide sequence encoding said protein can hybridize to the nucleic acid sequence of FIG. 1C under stringent conditions, or (3) a fragment of CTGF or a derivative thereof.

As used in this Specification, the term "induce," as used herein, shall mean to produce, form, to cause to produce, or to cause to form.

As used in this Specification, the phrase "induction agent" shall mean an agent, including proteins or other biological materials, which causes the production or formation of a specific end result (e.g., the production of connective tissue).

As used in this Specification, the term "polynucleotide" denotes DNA, cDNA and/or RNA which encode untranslated sequences which flank the structural gene encoding CTGF. For example, a polynucleotide of the invention includes 5' regulatory nucleotide sequences and 3' untranslated sequences associated with the CTGF structural gene. A polynucleotide of the invention which includes the 5' and 3' untranslated region is illustrated in FIG. 1C. The 5' regulatory region, including the promoter, is illustrated in FIG. 1B. A more detailed description of the polynucleotides contemplated by the present invention may be found at U.S. Pat. No. 5,408,040.

As used in this Specification, the phrase "stringent conditions" as used herein, refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

As used in this Specification, the phrase "recombinant expression vector" refers to a plasmid, virus or other vehicle known in the art that has been manipulated by insertion or incorporation of the CTGF genetic sequences.

As used in this Specification, the phrase "therapeutically effective" means that amount of CTGF which is effective in inducing bone or cartilage formation or wound healing.

6. BRIEF DESCRIPTION OF THE DRAWINGS

FIG. 1A shows the structural organization of the CTGF gene. Exons are indicated by boxed regions, with solid areas in the gene corresponding to the open reading frame.

FIGS. 1B1–1B2 show a comparison of nucleotide sequences bewteen CTGF promoter and fisp-12 promoter. Identical nucleotides are marked with asterisks. The TATA box and other consensus sequences are indicated and shaded. The site of transcriptional initiation is indicated at position number +1.

FIGS. 1C1, 1C2, 1C3 show the complete nucleotide and deduced amino acid sequence for the CTGF structural gene and 5' and 3' untranslated sequences.

FIG. 2 shows experimental in situ hybridization results related to the expression of CTGF transcripts in the growth plate of-long bones in newborn mice. The in situ hybridization experiments were performed using an anti-sense CTGF RNA probe as described below. Chondrocytes in the proliferation zone are strongly positive for CTGF gene expression, indicating that CTGF is produced at sites of cartilage growth.

FIG. 3 shows the expression of the CTGF gene during embryogenesis wherein a transgenic mouse is constructed using a fusion gene constructed from a CTGF promoter and a β-galactosidase structural gene. This gene, introduced into the germ line, expresses β-galactosidase at sites of CTGF expression and can be detected by histochemical means by expressing sections of the developing transgenic animal to the substrate X-gal which deposits a blue color at sites of β-galactosidase activity. Panel A is a 12 day mouse embryo from such a transgenic mouse. The blue staining is an area destined to become Meckel's cartilage, which is the first cartilage to form. Panel B is a photograph of the hind limb and paw which demonstrates staining at the ends of the long bones and in the paw in the growth plates of the metatarsal.

FIG. 4 provides evidence of induction of cartilage and bone in cultures of C3H10T1/2 mouse embryonic stem cells. C3H10T1/2 cells were cultured as described under methods. Cells were treated with either nothing (Panel A), 5-azacytodine (Panel B), CTGF at 50 ng/ml (Panel C) or 5-azacytodine followed by CTGF (Panel D).

FIG. 5 sets forth Northern blot analysis of CTGF gene expression in wound chambers implanted at sites of bone regeneration.

FIG. 6 sets forth evidence related to the expression of CTGF in human osteoblasts in response to TGF-β.

FIGS. 7A–7D set forth results of a chondrogenic assay.

FIG. 7A provides the chondrogenic assay results for the control culture.

FIG. 7B provides the chondrogenic assay results for a culture in which 5 ng/ml TGF-β1 was added.

FIG. 7C provides the chondrogenic assay results for a culture in which 5 ng/ml TGF-β1 and 10 ng cholera toxin were added.

FIG. 7D provides the chondrogenic assay results for a culture in which 5 ng/ml TGF-β1, 10 ng/ml cholera toxin, and 5 ng/ml CTGF were added.

Figure 2:
Figure 3A:
Figure 3B:
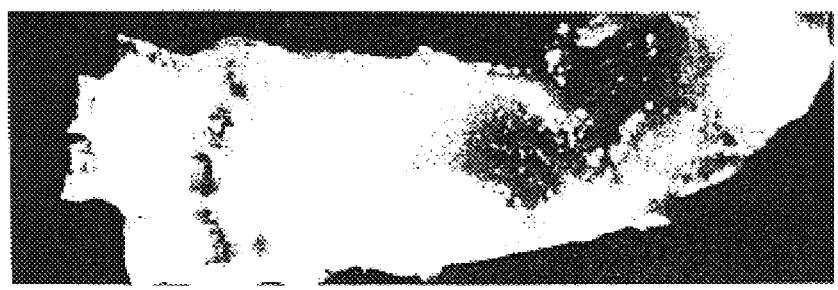
Figure 4A:
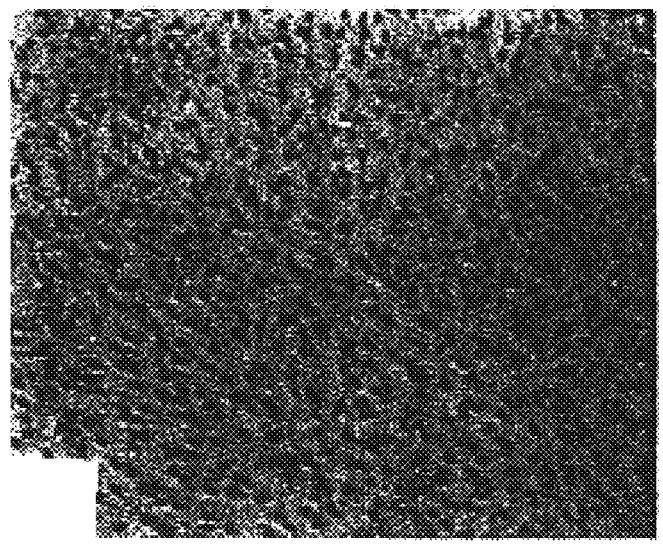
Figure 4B:
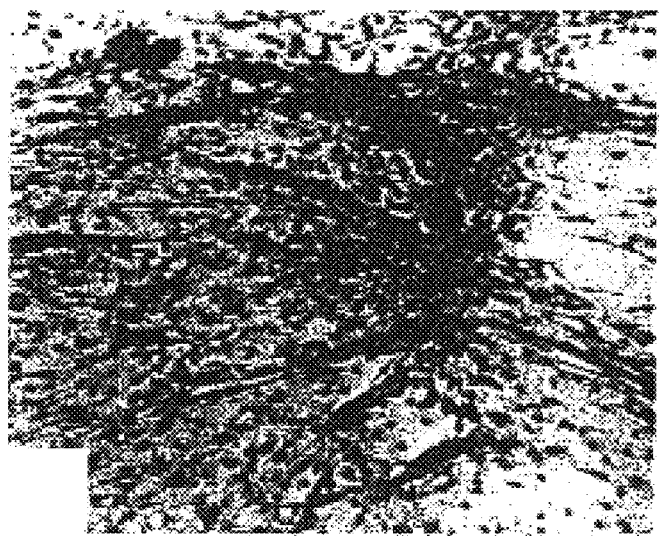
Figure 4C:
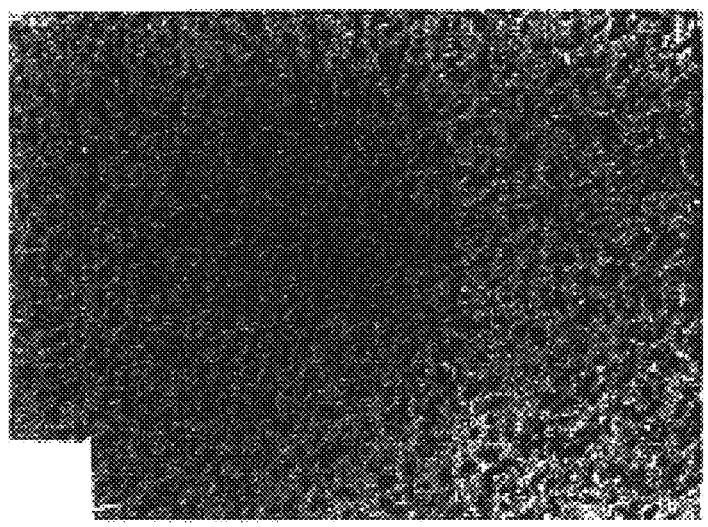
Figure 4D:

7. DETAILED DESCRIPTION OF THE INVENTION 7.1. Methods For Making CTGF

Nucleic Acid Sequences Encoding CTGF. In accordance with the invention, nucleotide sequences encoding CTGF or functional equivalents thereof may be used to generate recombinant DNA molecules that direct the expression of the protein or a functional equivalent thereof, in appropriate host cells. Alternatively, nucleotide sequences which hybridize, under stringent position, to portions of the CTGF sequence may also be used in nucleic acid hybridization assays, Southern and Northern blot analyses, etc. In yet another method, DNA molecules encoding CTGF may be isolated by hybridization procedures comprising antibody screening of expression libraries to detect shared structural features.

Due to the inherent degeneracy of the genetic code, other DNA sequences which encode substantially the same or a functionally equivalent amino acid sequence, may be isolated and used in the practice of the invention for the cloning and expression of CTGF. Such DNA sequences include those which are capable of hybridizing to the human CTGF sequence under stringent. conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the CTGF sequence, which result in a silent change thus producing a functionally equivalent protein. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, analine; asparagine, glutamine; serine, threonine; phenylalanine, tyrosine.

The DNA sequences of the invention may be engineered in order to alter the protein's sequence for a variety of ends including but not limited to alterations which modify processing and expression of the gene product. For example, mutations may be introduced using techniques which are well known in the art, e.g., site-directed mutagenesis to, for example, insert new restriction sites. For example, in certain expression systems such as yeast, host cells may overglycosylate the gene product. When using such expression systems it may be preferable to alter CTGF coding sequence to eliminate any N-linked glycosylation site.

The CTGF sequence may be ligated to a heterologous sequence to encode a fusion protein. For example, for screening of peptide libraries it may be useful to encode a chimeric CTGF protein expressing a heterologous epitope that is recognized by a commercially available antibody. A fusion protein may also be engineered to contain a cleavage site located between the CTGF sequence and the heterologous protein sequence (e.g. a sequence encoding a growth factor related to PDGF), so that CTGF can be cleaved away from the heterologous moiety.

The coding sequence of CTGF may also be synthesized in whole or in part, using chemical methods well known in the art. See, for example, Caruthers, et al., 1980, *Nucleic Acids Res. Symp. Ser.* 7:215–233; Crea and Horn, 1980, *Nucleic Acids Res.* 9(10):2331; Matteucci and Caruthers, 1980, *Tetrahedron Letters* 21:719; and Chow and Kempe, 1981, *Nucleic Acids Res.* 9(12):2807–2817. Alternatively, the protein itself could be produced using chemical methods to synthesize the CTGF amino acid sequence in whole or in part. For example, peptides can be synthesized by solid phase techniques, cleaved from the resin, and purified by preparative high performance liquid chromatography. See e.g., Creighton, 1983, *Proteins Structures And Molecular Principles*, W. H. Freeman and Co., N.Y. pp. 50–60. The composition of the synthetic peptides may be confirmed by amino acid analysis or sequencing. See e.g., for the Edman degradation procedure, see, Creighton, 1983, *Proteins, Structures and Molecular Principles*, W. H. Freeman and Co., N.Y., pp. 34–49.

A more detailed description of the nucleic acid sequences comprising the present invention and methods for identifying such sequences may be found in U.S. Pat. Ser. No. 5,408,040, which is incorporated herein by reference.

Expression Of CTGF. In order to express a biologically active CTGF, the nucleotide sequence coding for the protein, or a functional equivalent as described above, supra, was inserted into an appropriate expression vector, i.e., a vector which contains the necessary elements for the transcription and translation of the inserted coding sequence.

More specifically, methods which are well known to those skilled in the art can be used to construct expression vectors containing the CTGF sequence and appropriate transcriptional/translational control signals. These methods include in vitro recombinant DNA techniques, synthetic techniques and in vivo recombination/genetic recombination. See e.g., the techniques described in Maniatis et al., 1989, Molecular Cloning: A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the CTGF coding sequence. These include but are not limited to microorganisms such as bacteria transformed with recombinant bacteriophage DNA, plasmid DNA or cosmid DNA expression vectors containing the CTGF coding sequence; yeast, including *Pichia pastoris* and *Hansenula polymorpha*, transformed with recombinant expression vectors containing the CTGF coding sequence; insect cell systems infected with recombinant virus expression vectors (e.g., bacculovirus) containing the CTGF coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the CTGF coding sequence; or animal cell systems infected with recombinant virus expression vectors (e.g., adenovirus, vaccinia virus, human tumor cells (including HT-1080)) including cell lines engineered to contain multiple copies of the CTGF DNA either stably amplified (CHO/dhfr) or unstably amplified in double-minute chromosomes (e.g., murine cell lines). As used herein, it is understood that the term "host-expression vector systems" and more generally, the term "host cells" includes any progeny of the host cell or host-expression vector system. It is further understood that although all progeny may not be identical to the parental cell, as mutations may occur during replication, such progeny are included in the scope of the invention.

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in-insect cell systems, promoters such as the bacculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the CTGF DNA SV40-, BPV- and EBV-based vectors may be used with an appropriate selectable marker.

In bacterial systems, a number of expression vectors may be advantageously selected depending upon the use intended for the expressed CTGF. For example, a suitable vector for expression in bacteria includes the T7-based vector as described in Rosenberg, et al., 1987, *Gene* 56:125. As further example, when large quantities of CTGF are to be produced to screen peptide libraries, vectors which direct the expression of high levels of protein products that are readily purified may be desirable. Such vectors include but are not limited to the E. coli expression vector pUR278 (Ruther et al., 1983, *EMBO J.* 2:1791), in which the CTGF coding sequence may be ligated into the vector in frame with the lac Z coding region so that a hybrid AS-lac Z protein is produced; pIN vectors (Inouye & Inouye, 1985, *Nucleic Acids Res.* 13:3101–3109; Van Heeke & Schuster, 1989, *J. Biol. Chem.* 264:5503–5509); and the like. pGEX vectors may also be used to express foreign polypeptides such as CTGF with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

More generally, where the host is a procarote, competent cells which are capable of DNA uptake can be prepared from cells harvested after exponential growth and subsequently treated by the $CaCl_2$, or alternatively $MgCl_2$ or RbCl, method using procedures well known in the art.

Where the host cell is a eucaryote, various methods of DNA transfer can be used. These include transfection of DNA by calcium phosphate-precipitates, conventional mechanical procedures, including microinjection, insertion of a plasmid encased in liposomes, or use of virus vectors. Eucaryotic cells may also be cotransformed with DNA sequences encoding the polypeptide of the invention, and a second foreign DNA molecule encoding a selectable phenotype, such as herpes simplex thymidine kinase gene. Another method is to use a eukaryotic viral vector, such as simian virus 40 (SV40) or bovine papilloma virus, to transiently infect or transform eucaryotic cells and express protein. See, Eukaryotic Viral Vectors, 1992, Cold Spring Harbor Laboratory, Gluzman, Ed.). Eucaryotic host cells include yeast, mammalian cells, insect cells and plant cells.

In yeast, a number of vectors containing constitutive or inducible promoters may be used. For a review see, *Current Protocols in Molecular Biology*, Vol. 2, 1988, Ausubel et al., Ed., Greene Publish. Assoc. & Wiley Interscience, Ch. 13; Grant et al., 1987, Methods in Enzymology, Wu & Grossman, Eds., Acad. Press, N.Y., 153:516–544; Glover, 1986, DNA Cloning, Vol. II, IRL Press, Wash., D.C., Ch. 3; Bitter, 1987, Heterologous Gene Expression in Yeast, Methods in Enzymology, Berger & Kimmel, Eds., Acad. Press, N.Y., 152:673–684; and The Molecular Biology of the Yeast Saccharomyces, 1982, Strathern et al., Eds., Cold Spring Harbor Press, Vols. I and II. For example, various shuttle vectors for the expression of foreign genes in yeast have been reported. Heinemann, et al., 1989, *Nature* 340:205; Rose, et al., 1987, *Gene* 60:237.

In cases where plant expression vectors are used, the expression of the CTGF coding sequence may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843); or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques, see, e.g., Weissbach & Weissbach, 1988, Methods for Plant Molecular Biology, Academic Press, NY, Section VIII, pp. 421–463; Grierson & Corey, 1988, Plant Molecular Biology, 2d Ed., Blackie, London, Ch. 7–9.

In an insect system, an alternative expression system could be used to express CTGF. In one such system, Bacculovirus is used as a vector to express foreign genes. The virus then grows in the insect cells. The CTGF coding sequence may be cloned into non-essential regions (for example the polyhedrin gene) of the virus and placed under control of a Bacculovirus promoter. These recombinant viruses are then used to infect insect cells in which the inserted gene is expressed. See, e.g., Smith et al., 1983, *J. Virol.* 46:584; Smith, U.S. Pat. No. 4,215,051.

In mammalian host cells, a number of viral based expression systems may be utilized. In cases where an adenovirus is used as an expression vector, the CTGF coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing CTGF in infected hosts. See e.g., Logan & Shenk, 1984, *Proc. Nat. Acad. Sci. (USA)* 81:3655–3659. Alternatively, the vaccinia 7.5K promoter may be used. See, e.g., Mackett et al., 1982, *Proc. Natl. Acad. Sci. (USA)* 79:7415–7419; Mackett et al., 1984, *J. Virol.* 49:857–864; Panicali et al., 1982, *Proc. Natl. Acad. Sci.* 79:4927–4931.

In another embodiment, the CTGF sequence is expressed in human tumor cells, such as HT-1080, which have been stably transfected with calcium phosphate precipitation and a neomycin resistance gene. In yet another embodiment, the PMSXND expression vector or the like is used for expression in a variety of mammalian cells, including COS, BHK 293 and CHO cells. Lee and Nathans, 1988, *J. Biol. Chem.* 263:3521.

Specific initiation signals may also be required for efficient translation of inserted CTGF coding sequences. These signals include the ATG initiation codon and adjacent sequences. In cases where the entire CTGF gene, including its own initiation codon and adjacent sequences, is inserted into the appropriate expression vector, no additional translational control signals may be needed. However, in cases where only a portion of the CTGF coding sequence is inserted, exogenous translational control signals, including the ATG initiation codon, must be provided. Furthermore, the initiation codon must be in phase with the reading frame of the CTGF coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. See e.g., Bitter et al., 1987, *Methods in Enzymol.* 153:516–544.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important-for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, HT-1080 etc.

For long-term, high-yield production of recombinant proteins, stable expression is preferred. For example, cell lines which stably express CTGF may be engineered. Rather than using expression vectors which contain viral origins of replication, host cells can be transformed with CTGF DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Acad. Sci. (USA)* 48:2026), and adenine phosphoribosyltransferase (Lowy, et al., 1980, *Cell* 22:817) genes can be employed in tk–, hgprt– or aprt– cells, respectively.

Also, antimetabolite resistance can be used as the basis of selection for dhfr, which confers resistance to methotrexate (Wigler, et al., 1980, *Proc. Natl. Acad. Sci. (USA)* 77:3567; O'Hare, et al., 1981, *Proc. Natl. Acad. Sci. (USA)* 78:1527); gpt, which confers resistance to mycophenolic acid. (Mulligan & Berg, 1981, *Proc. Natl. Acad. Sci. (USA)* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147) genes. Recently, additional selectable genes have been described, namely trpB, which allows cells to utilize indole in place of tryptophan; hisD, which allows cells to utilize histinol in place of histidine (Hartman & Mulligan, 1988, *Proc. Natl. Acad. Sci. (USA)* 10 85:8047), and ODC (ornithine decarboxylase) which confers resistance to the ornithine decarboxylase inhibitor, 2-(difluoromethyl)-DL-ornithine, DFMO (McConlogue, 1987, *In: Current Communications in Molecular Biology*, Cold Spring Harbor Laboratory ).

The isolation and purification of host cell expressed polypeptides of the invention may be by any conventional means such as, for example, preparative chromatographic separations and immunological separations such as those involving the use of monoclonal or polyclonal antibody.

7.2. Identification of Transfectants or Transformants that Express CTGF

The host cells which contain the coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of CTGF MRNA transcripts in the host cell; and (d) detection of the gene product as measured by an assay or by its biological activity.

In the first approach, the presence of the CTGF coding sequence inserted in the expression vector can be detected by DNA-DNA or DNA-RNA hybridization using probes comprising nucleotide sequences that are homologous to the CTGF coding sequence, respectively, or portions or derivatives thereof.

In the second approach, the recombinant expression vector/host system can be identified and selected based upon the presence or absence of certain "marker" gene functions (e.g., resistance to antibiotics, resistance to methotrexate, transformation phenotype, occlusion body formation in bacculovirus, etc.). For example, in a preferred embodiment, the CTGF coding sequence is inserted within a neomycin-resistance marker gene sequence of the vector, and recombinants containing the CTGF coding sequence can be identified by the absence of the marker gene function. Alternatively, a marker gene can be placed in tandem with the CTGF sequence under the control of the same or different promoter used to control the expression of the CTGF coding sequence. Expression of the marker in response to induction or selection indicates expression of the CTGF coding sequence.

In the third approach, transcriptional activity for the CTGF coding region can be assessed by hybridization assays. For example, RNA can be isolated and analyzed by Northern blot using a probe homologous to the CTGF coding sequence or particular portions thereof. Alternatively, total nucleic acids of the host cell may be extracted and assayed for hybridization to such probes.

The fourth approach involves the detection of the biologically active or immunologically reactive CTGF gene product. A number of assays can be used to detect CTGF activity including but not limited to those assays described in U.S. Pat. No. 5,408,040.

7.3. Treatment Indications

The methods, compounds and formulations of the present invention are each directed to the treatment of disorders, diseases or ailments related to the underproduction of connective tissue in bone, cartilage, or other organs such as skin and muscle alternatively, to disorders, diseases or ailments in which the formation of bone or cartilage is desired.

These diseases, disorders or ailments include the repair of cartilage or bone defect after a variety of traumatic injuries or disorders including arthritis, osteoporosis and other skeletal disorders, hypertrophic scars, burns, and vascular hypertrophy. Because these problems are due to a poor growth response of the fibroblasts, stem cells, chondrocytes, osteoblasts or fibroblasts at the site of injury, the addition of a biologically active agent which could stimulate the growth of these cells would be beneficial.

Another important use of CTGF would be in culture systems to expand stem cells or chondrocytes that were removed from an individual prior to reimplantation. In a similar process, CTGF could be added to either stem cells or chondrocytes when they were to be added as a graft to help stimulate the expansion and differentiation of these cells at the site of implantation. CTGF could also be added to a graft composed of cartilage or bone to help stimulate growth.

Another treatment indication is directed to administering CTGF to a patient in need to enhance wound healing. PDGF and other growth factors, such as CTGF, are involved in normal healing of skin wounds. The CTGF polypeptide of this invention is valuable as a therapeutic in cases in which there is impaired healing of skin wounds or there is a need to augment the normal healing mechanisms, e.g., burns. One important advantage to using CTGF protein to accelerate wound healing is attributable to the molecule's high percentage of cysteine residues. CTGF, or functional fragments thereof, is more stable and less susceptible to protease degradation than PDGF and other growth factors known to be involved in wound healing.

Preferably, the agent of this invention is the combination of TGF-$\beta$ and CTGF, however, it is likely that other TGF-$\beta$ family members will also be useful in accelerating wound healing by inducing CTGF. The composition of the invention aids in healing the wound, in part, by promoting the growth of connective tissue. The composition is prepared by combining, in a pharmaceutically acceptable carrier substance, e.g., inert gels or liquids, the purified CTGF and TGF-$\beta$.

The treatment indications, with respect to wound healing, contemplated by this invention include anticipated wounds (i.e. wounds resulting from surgical procedures), as well as unanticipated wounds (i.e. wounds caused by trauma).

7.4. Pharmaceutical Formulations and Routes of Administration

The molecules of the present invention can be administered to a patient in need, by itself, or in pharmaceutical compositions where one or more of the molecules are mixed with suitable carriers or excipient(s) at doses to treat or ameliorate a variety of disorders. Alternatively, as CTGF is produced by endothelial cells and fibroblastic cells, both of which are present at the site of bone or cartilage formation and wounding, agents which stimulate the production of CTGF can be added to a composition which is used to accelerate bone or cartilage induction or wound healing. Preferably, the agent of this invention is transforming growth factor beta. The composition of the invention aids in healing the wound, in part, by promoting the growth of connective tissue. In another embodiment, CTGF may be administered in combination with proteins or compounds which are believed to promote the formation of connective tissue.

Whether the composition is comprised of CTGF alone or CTGF and additional agents as the active ingredient, such composition is prepared by combining, in a pharmaceutically acceptable carrier substance, e.g., inert gels or liquids, the purified CTGF and TGF-$\beta$.

A therapeutically effective dose further refers to that amount of the compound sufficient to result in amelioration of symptoms. Techniques for formulation and administration of the compounds of the instant application may be found in "Remington's Pharmaceutical Sciences," Mack Publishing Co., Easton, Pa., latest edition.

7.4.1. Routes Of Administration.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an area requiring CTGF, often in a depot or sustained release formulation.

Furthermore, one may administer the drug in a targeted drug delivery system, for example, in a liposome coated with a specific antibody, targeting, for example, cartilage. The liposomes will be targeted to and taken up selectively by the afflicted tissue.

7.4.2. Composition/Formulation.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active molecules into preparations which can be used pharmaceutically. Proper formulation is dependent upon the route of administration chosen.

For injection, the agents of the invention may be formulated in aqueous solutions, preferably in physiologically-compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration,the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The molecules may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection-suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic molecules of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds-well,-and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic molecules may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

7.4.3. Effective Dosage.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal CTGF activity). Such information can be used to more accurately determine useful doses in humans.

A therapeutically effective dose refers to that amount of the molecule hat results in amelioration of symptoms or a prolongation of survival in a patient. Toxicity and therapeutic efficacy of such molecules can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Molecules which exhibit high therapeutic indices are preferred. The data obtained from these cell culture assays and animal studies can be used in formulating a range of dosage for use in human. The dosage of such molecules lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1.

Dosage amount and interval may be adjusted individually to provide plasma levels of the active moiety which are sufficient to maintain the induction effects of CTGF, or minimal effective concentration (MEC). The MEC will vary for each compound but can be estimated from in vitro data; for example, the concentration necessary to achieve 50–90% activity of CTGF to induce bone growth using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

7.4.4. Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of disorders or diseases in which cartilage or bone induction and wound healing, or the like is desired. PATENT 7.5 Identification of Compounds Which Induce the Production of CTGF in Cartilage and The identification of the promoter element of the CTGF gene and specifically, the TGF-β responsive/regulatory element (TβRE) (5'-GTGTCAACCCTC-3'; nucleotides −157 and −145), provides a source for a screening method for identifying compounds or compositions which affect the expression of CTGF. Specifically, the method by which compositions which enhance the activity of CTGF, and thereby may be used to enhance bone, tissue and cartilage induction may be identified, comprises: (1) incubating components such as, but not limited to, oligonucleotides comprising the composition and a TGF-β responsive element of the CTGF promoter, wherein said incubation is carried out under conditions sufficient to allow the components to interact; and (2) measuring the effect of the composition on CTGF expressi on. Preferably, the promoter region used in the screening assays described herein includes nucleotides −823 to +74, although smaller regions that include the TGF-β responsive element may also be useful in the disclosed method (e.g. −162 to −128, or −154 to −145). In other assays, nucleotides in this region including TβRE are coupled to a receptor gene such as luciferase and are transfected into mammalian cells to derive a cell line, bearing a construct and showing activity when incubated with TGF-β. These drugs, oligonucleotides, and chemicals in libraries that modify the activation can be readily detected in cell assays.

8. EXAMPLES

The connective tissue growth factor gene is not only express ed in fibroblasts but is selectively induced by TGF-β only in mesenchymally derived connective tissue cells (i.e., fibroblasts, smooth muscle, chondrocytes, osteoblasts, astroglial cells, etc.). The expression of the gene connective tissue cells that form the skeletal elements in vertebrates indicate that CTGF plays a role in the formation of cartilage, bone tendon and muscle in the vertebrate animal. The results of the following examples demonstrate that CTGF can regulate the induction, differentiation and growth of cells which form both cartilage and bone in vertebrate animals, including humans. Specifically, the results provide that: (1) CTGF transcripts are present in the growth plate of long bones in adult rats and newborn mice; (2) The CTGF gene is expressed at sites of cartilage induction and growth in embryonic mice; (3) CTGF receptors are present on rat chondrocytes; (4) The CTGF gene is expressed at site of bone regeneration after injury in adult rabbits; (5) The CTGF protein can induce pluripotent mouse embryonic stem cell lines to differentiate in to chondrocytes and osteoblasts; 6) Human osteoblasts produce CTGF in culture.

8.1 Biological Assays

Methods: Mitogenic And Anchorage Independent Growth Assays. Mitogenic assays were performed in monolayer cultures using 48 well plates and NRK fibroblasts as target cells as described previously in Grotendorst, et al. 1991, *J. Cell Physiol.* 149:235–243. Anchorage independent growth assays were performed essentially as described in Guadagno and Assoian, 1991, *J. Cell Biol.* 115:1572–1575.

Methods: Extracellular Matrix Protein mRNA Induction Assays. NRK rat fibroblasts were grown to confluence in Dulbecco's modified eagle media with 5% gfetal bovine serum and then serum starved in DMEM with 1% bovine serum albumin for 24 hours. Growth factors were added to the cell cultures and total cellular RNA was extracted after 24 hours and northern blot analysis was performed as described in Igarashi, et al., 1993, *Mol. Biol. Cell* 4:637–645.

To ensure that equivalent amounts of total RNA were added to each lane on a gel, RNA was quantitated by $A_{260/290}$ ratios and equivalent transfer was assured by comparing ribosomal 28S and 18S RNA bands in each lane after staining with ethidium bromide. As additional control, blots were reprobed with an actin cDNA probe. Double stranded cDNA fragments used for probes were labeled with $^{32}$P-dCTP using a random prime labeling kit (Boehringer Mannheim, Indianapolis, Ind.). The CTGF probe was derived from a 1.1 kb human cDNA fragment which encompassed the open reading frame of the CTGF transcript. The TGF-β1 probe was a 1.0 kb Nar I fragment derived from a 2.0 kb human TGF-β1 cDNA (G. I. Bell, H.H. Medical Institute, University of Chicago). The αI-type 1 human collagen probe was derived from a 1.5 kb ORF fragment at the 3' end (ATCC No. 61323). The α5 integrin probe was produced from a cDNA insert containing a portion of the human cDNA containing the open reading frame, as obtained by R. Associan at the University of Miami. The human fibronectin probe was a 0.9 kb EcoR1/HindIII fragment derived from a 2.2 kb cDNA clone containing the 3' region of the open reading frame provided by F. Woessner (also of University of Miami). The human actin probe, used as the control RNA probe, was purchased from Oncor, Co. (Gaithersberg, Md.).

8.2 Locus of CTGF Transcripts in Newborn Mice

Experiments were conducted to determine whether CTGF transcripts are present in the growth plate of long bones of newborn mice according to Fava, et al., 1990, *Blood* 76:1946–1955.

Method: In situ Hybridization. The tissue samples were immediately placed in 4.0% paraformaldehyde for 1.5 hours and then flash frozen and embedded. Sections were cut at 5 µm and placed on TESPA coated slides (Oncor, Gathersburg, Md.). In-situ hybridization for CTGF mRNA was performed using standard methods. Briefly, slides with specimens were hydrated through graded alcohols, treated with 20 µg/ml proteinase K in 50 mM Tris-HCl ph 7.4, 5 mM EDTA, refixed in 4.0% paraformaldehyde and dipped in 0.1 M triethanolamine and 1 ml acetic anhydride, prior to dehydration in sequentially graded alcohols. Both sense and antisense CTGF RNA probes were constructed using a riboprobe kit (Promega, Madison, Wis.) with T7 and Sp6 promoters, respectively. The specific activity of the probes was 1×108 cpm/µg RNA. Slides were hybridized overnight in 50% deionized formamide, 10% dextran sulfate, 50 mM DTT, 0.3M NaCl, 0.01 M Tris pH 7.5, 5 mM EDTA, 10 mM Na2HPO4, 0.02 % Ficoll, 0.02 % PVP, 0.02 % BSA, 0.2 mg/ml yeast tRNA and the riboprobe (5×104 cpm/µl) under a coverslip at 54° C. Slides were washed in 250 ml 5×SSC, 10 mM beta mercaptoethanol at 50° C. for 30 minutes, 2×SSC, 100 mM beta mercaptoethanol, 50% formamide at 65° C. for 20 minutes and 3 times in TEN buffer (1 M Tris, 0.5 M EDTA, 5M NaCl) for 10 minutes. The second TEN wash included 10 µg RNase A. The final two washes were in 2×SSC at 65° C. for 15 minutes each. After dehydrating again through graded alcohols with 0.3 M ammonium acetate, the slides were dipped in photographic emulsion (Ilford K-5, Polyscience) and incubated for 8 days at 40° C. Slides were then developed and sections counter stained in Mayer's hematoxylin and eosin.

Results. The results of these studies indicate that the CTGF gene is expressed in the proliferation zone of the growth plate. This zone contains the chrondrocytes that are actively replicating to increase the length of the bone. The expression of CTGF at this site is consistent with it functioning as a growth factor for the chondrocytes.

8.3 CTGF Gene Expression at Site of Cartilage Induction and Growth in Embryonic Mice.

In order to confirm CTGFs role in cartilage induction and growth, the expression of the CTGF gene in mouse embryo's at sites where cartilage and bone will form but have not formed yet was studied. For purposes of this study, a transgenic mouse line which contains a transgene composed of the human CTGF promoter elements which are regulating the expression of the bacterial β-galactosidase gene. Cells that express this gene can be readily identified by staining using X-gal which forms a blue colored precipitate at the sites of enzymatic activity. Using this methodology we stained embryo's from transgenic mice to localize the expression of the CTGF gene. As set forth at FIG. 4, Panel A, no cartilage or bone was formed, indicating the CTGF is expressed prior to the formation of the skeleton and could function as the inducer of cartilage and bone. These results further demonstrate that the expression of the transgene corresponds with the expression detected by in situ hybridization using the CTGF probe.

These studies also demonstrate that the gene is expressed at growth plates in the long bone, in precartilaginous zones and in Meckel's cartilage, the first cartilage to form during mammalian development. These areas are referred to as prechondrogenic mesenchyme and are distinguished by condensations of the cells. The CTGF gene is expressed in these sites but not in adjacent tissue. Furthermore, the CTGF gene is expressed at these sites 1 day prior to the condensation which occurs 1 day prior to the actual formation of the cartilage. These findings demonstrate that CTGF is present prior to the formation of cartilage or cells with a true chondrocytic phenotype, and is consistent with CTGF acting to induce the cartilage phenotype in undifferentiated stem cells.

Importantly, these studies demonstrate that CTGF is expressed at sites in the embryo that form bone by either the intramembranous, or endochondral pathways, demonstrating that it can function as a signal for cartilage development from either non-differentiated mesenchymal stem cells which form the bones of the limbs, or neural crest cells which form the cartilage in Meckel's cartilage and the bones of the skull.

8.4 Loci Of CTGF Receptors On Rat Chondrocytes

In order for cells to respond to peptide factors such as CTGF, they must express on their surface the cognate receptor for the specific peptide factor.

Figure 8A:
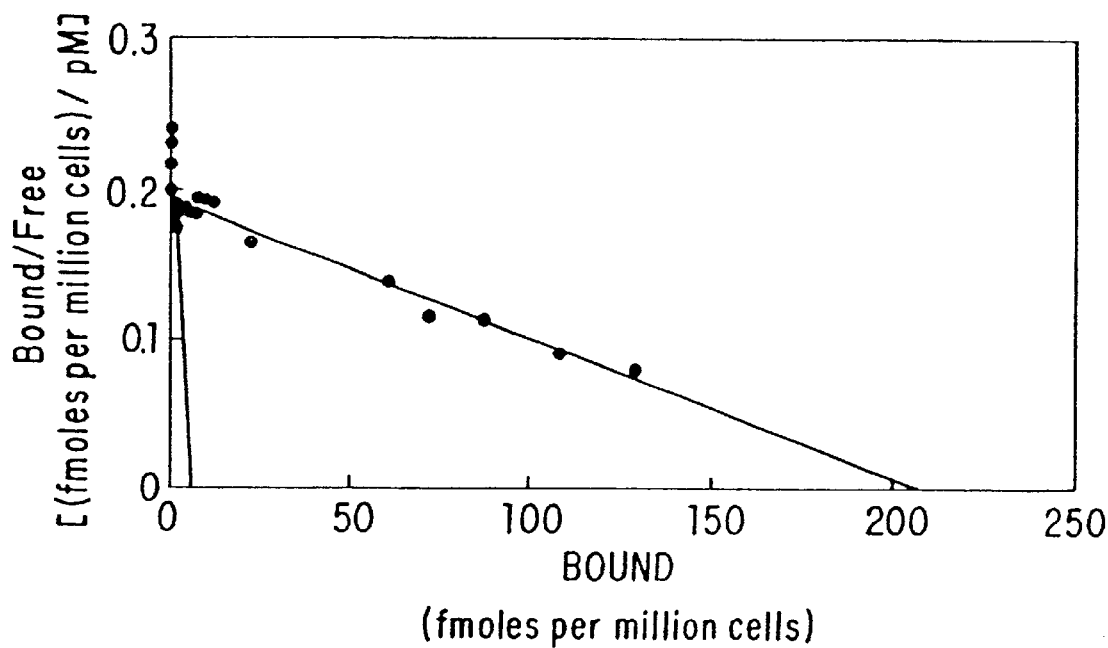
FIG. 8A is a Scatchard Plot reflecting CTGF binding to NRK cells.
Figure 8B:
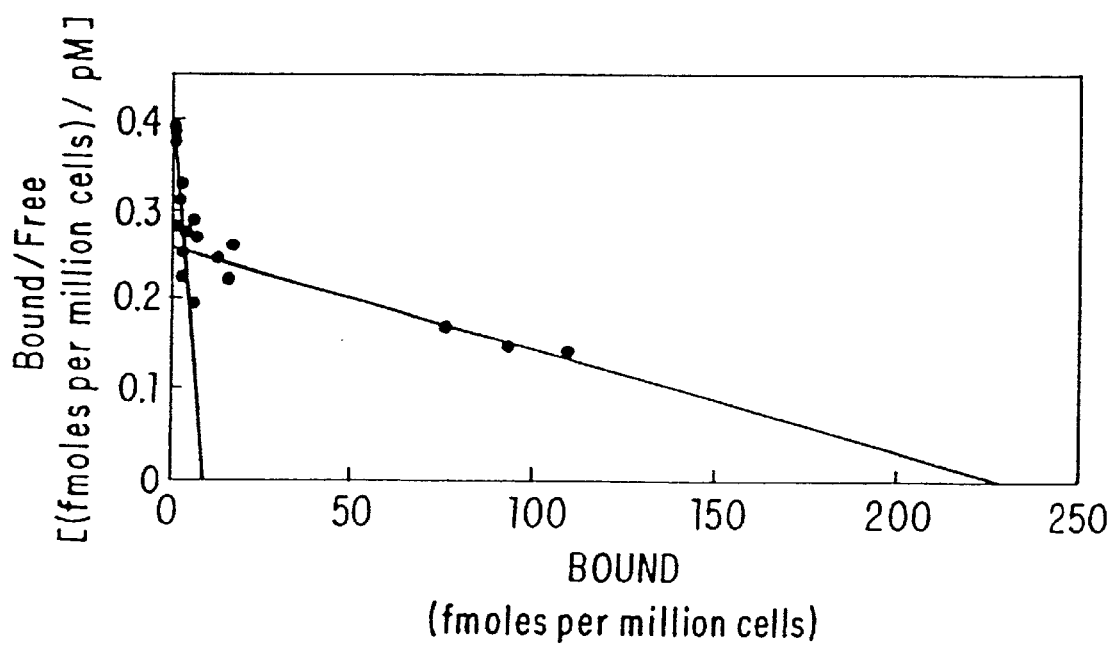
FIG. 8B is a Sctachard Plot reflecting CTGF binding to rat chondroblasts.

Equilibrium Assay. Equilibrium binding assays were performed on confluent monolayers of NRK-49F rat fibroblasts and primary rat articular chondroblasts to determine the number and affinity of CTGF receptors on these cells. Binding was performed in the cold for 4 hours with varying concentrations of iodinated recombinant human CTGF (rhCTGF). Non-specific binding was determined by including a 200-fold molar excess of unlabeled ligand. Representative Scatchard plots are set forth at FIG. 8A (with respect to equilibrium binding assays performed using NRK cells) and FIG. 8B (with respect to equilibrium binding assays performed using rat chondroblasts).

Competition Assay. Several cell types were tested for the expression of CTGF receptors including, normal rat kidney fibroblasts, mouse fibroblasts, mink lung epithelial cells and rat articular chondrocytes. CTGF was labeled by iodination with $^{125}I$ and the radiolabeled CTGF used in competition binding assays to measure CTGF receptors on the various cell types. As set forth in Table 1, below, only the NRK fibroblasts and rat articular chondrocytes expressed high affinity receptors for CTGF. Mouse fibroblasts had few if any high affinity receptors and no binding was detected in the mink lung epithelial cells.

TABLE 1

BINDINC CHARACTERISTIC FOR rhCTGF ON VARIOUS CELLS

| Cell Type | High Affinity | | Low Affinity | |
| --- | --- | --- | --- | --- |
| | KD (pM) | Sites/cell | KD (nM) | Sites/cell |
| NRK | 13–23 | 2200–3500 | 1.1–2.2 | 126,000–195,000 |
| Chondrocytes | 21 | 3500–4800 | 1.0 | 150,000 |
| NTH3T3 | 5–10 | 480 | 1.8 | 102,000 |
| MLEC | none detected | | none detected | |

These data indicate that chondrocytes express both CTGF and its receptor and would are therefore capable of responding to CTGF as a growth stimulatory factor.

8.5 CTGF Activity in Inducing Pluripotent Mouse Embryonic Stem Cell Lines to Differentiate into Chondrocytes and Osteoblasts.

The ability of CTGF to induce the chondrocytic and osteocytic phenotype in undifferentiated stem cells in cell culture was evaluated. Specifically, the cell line C3H10Tl/2 was used to evaluate this biological activity. These cells are a standard and well established line for these types of investigations. The C3H10Tl/2 can be maintained in an undifferentiated state in culture, and then induced to differentiate into skeletal muscle cells, chondrocytes, osteoblasts and adipocytes. Cells treated with CTGF formed colonies of chondocytes and cartilaginous nodules. Cells treated overnight with 5-azacytodine overnight followed by treatment with CTGF differentiated into osteoblasts and osteoid bodies. The differentiation of these cultures into muscle and adipocytes was blocked by the presence of CTGF.

More specifically, the cells were treated overnight with 5 azacytodine followed by a 10–14 day incubation to allow for the differentiation to occur. The effects of 5 azacytodine and CTGF alone and in combination on these cell were then compared. Control cultures which were not treated with either agent remained as undifferentiated cells in monolayer. As set forth as FIG. 4, cultures treated with 5azacytodine alone differentiated into primarily skeletal muscle cells (myotubes) and adipocytes. No chondrocytes could be found in the cultures. CTGF treatment of the cultures (50 ng/ml) for 10 days resulted in the induction of cartilaginous nodules. These nodules were not found under any other conditions. Treatment of the cultures with FGF, PDGF, EGF or TGF-β did not induce these nodules indicating that CTGF is uniquely capable of inducing cartilage in the undifferentiated mesenchymal stem cells.

Treatment of the cells with both 5 azacytodine (overnight) followed by a 10 day exposure to CTGF (50 ng/ml) had a significant effect on the cultures. First, no skeletal myotubes where present demonstrating that CTGF prevented the cells from differentiating into skeletal muscle cells. Second, while some cartilaginous nodules were present most of the nodules appeared to be osteoid (bone). Thus, CTGF can induce the formation of both chondrocytes and osteoblasts from undifferentiated mesenchymal cells. These results demonstrate that this factor could be used to stimulate the differentiation of cartilage and bone where desired.

8.6 CTGF Gene Expression at Site of Bone Regeneration after Injury in Adult Rabbits.

An experimental model was developed to examine the expression of various regulatory and matrix protein genes during wound repair. In this model, mesh nylon cylinders are implanted in the ilium of the pelvis of male New Zealand white rabbits (10 kg) which had been anesthetized by ether. A 1.1 cm diameter hole was bored in the ilium of the pelvis using a bone trephine and the chamber press fit into the hole. The chamber was anchored in place using flaps of the adjacent musculature and ligaments. Two chambers were implanted in each of twenty animals.

Animals were sacrificed on Days 9, 14, 21, 24, 28, 31, 35, 42 and 56 after implantation of the chambers. The chambers were removed and the tissue on the outside of the chambers were carefully and completely removed. The chambers were then cut open and tissue contained within the chambers was collected.

Total RNA was extracted from the tissue obtained from 6–18 chambers (pooled from 1–3 animals) by Guanidine-isothiocynate extraction (Chomcaynski and Sacchi, 1987, *Anal. Biochem.* 162:156–159) and CsCl centrifugation (Chirgwin, et al., 1979, *Biochemistry* 18:5294–5299). The amount of RNA recovered ranged from 100–300μg during the different days of collection. Total RNA was electrophoresed on an agarose/formaldehyde gel and transferred to nitrocellulose. Equivalent amounts of RNA were transferred as judged from staining of the ribosomal RNA present in each sample on the nitrocellulose filter. The CTGF probe was a 900 base pair fragment which represented the open reading frame of the CTGF cDNA. Hybridizations were performed using $1 \times 10^6$ cpm/ml of these probes labeled with [$P^{32}$]dCTP by using a Random Primer DNA Labeling Kit (Boehringer Mannheim Biochemicals, Indianapolis, Ind.). Autoradiography was performed at −70° C. for 24–72 hours by using X-ray films and intensifying screens.

The tissue proceeded through a regular cascade of repair where blood coagulation is followed by inflammation and then connective tissue in growth. In the bone implanted chambers the dense connective tissue which formed was similar if not indistinguishable from that which forms in soft tissue implants.

Figure 5:
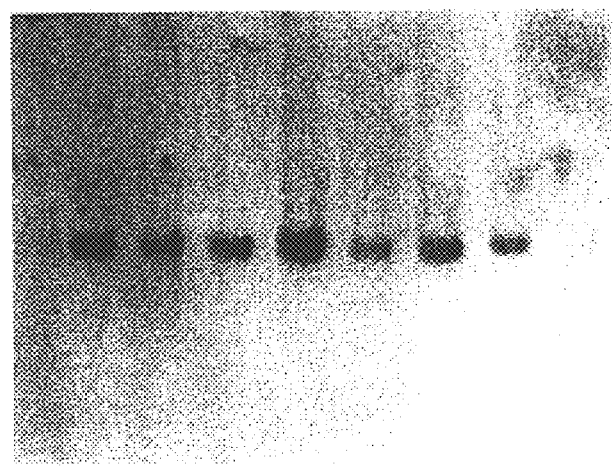
Figure 6:

As set forth in FIG. 5, CTGF gene expression is evident from Days 14–42. This is 4 days prior to the first histological appearance of bone within the chambers and coincides with the time course for the formation of bone within the chambers. However, as also set forth at FIG. 5, around day 17–18 post-implantation there were some changes in the morphology of areas of the connective tissue. These areas then began to form bone by day 20–21 post-implantation, demonstrating that this is a functional model for the study of bone regeneration.

The expression of CTGF MRNA in the chambers preceded slightly and then coincided with the formation and growth of the osteogenic areas within the chamber, demonstrating that CTGF is expressed at sites of bone regeneration in mammals.

8.7 Human Osteoblast Formation by Administration of CTGF

Cell culture. Human osteoblasts were grown from explants of human bone. Cells were cultured in Dulbecco's modified Eagle's medium (DMEM) containing 10% fetal calf serum (FCS) at 37° C. in an atmosphere of 10% $CO_2$ and 90% air.

Western blot analysis. CTGF content in conditioned media was analyzed by SDS-PAGE on 12% acrylamide gels followed by transfer to nitrocellulose filters using electroblotting. The blots were incubated for 1 hour in Tris-buffered saline (100 mM NaCl, 50mM Tris-HCl pH7.4) with 2 % nonfat powdered milk (TBS-milk), prior to overnight exposure to 2 g/ml chicken anti-human CTGF IgY diluted in TBS-milk. Filters were washed five times in TBS-milk, 5 minutes each, and incubated with alkaline-phosphatase-conjugated affinity purified rabbit anti-chicken IgY (1:1,000 dilution, Organon Teknika-Cappel, West Chester, Pa.) in TBS-milk for 90 minutes. The filters were washed three times with TBS-milk followed by two washes in TBS, and the antigens were detected using a commercial alkaline phosphatase substrate kit (Sigma, St. Louis, Mo.).

Results. Human osteoblasts were obtained from donors after surgical removal of bone during procedures to remove bone tumors or joint replacement. Osteoblasts were cultured from the bone and identified using standard. Cells were grown to confluence in complete media containing 10% fetal calf serum and made quiescent by changing the media to serum free media overnight. Some cultures were treated with TGF-$\beta$ and compared to non-treated cultures. The osteoblast that were treated with TGF-$\beta$ were stimulated to produce CTGF, as detected with a specific anti-CTGF antibody. As set forth at FIG. 5, the media was collected and analyzed for CTGF production and secretion by immunopurification of the CTGF with a CTGF specific antibody and detection and quantitation by western blots using the same antibody. As observed with fibroblasts, smooth muscle cells, and chondrocytes, TGF-$\beta$ induces CTGF production by the human osteoblasts. Control non-treated cells did not synthesis detectable amounts of CTGF.

As evidenced by this experiment, osteoblasts respond to TGF-$\beta$ similarly to other connective tissue cells with regard to CTGF production.

8.8 Transgenic Rabbit Models

All mice studies were conducted in accordance with the principles and procedures outlined in "Guidelines for Care and Use of Experimental Animals". Generation of transgenic models was carried out at the University of Miami Transgenic Mouse Core Facility using standard techniques. Briefly, the gene to be injected (transgene) was linearized by restriction digestion and the DNA fragment isolated by low melt agarose gel electrophoresis and purified using the GENECLEAN system (Qbiogene, Carlsbad Calif.).

Transgenic mice were generated by injecting linearized DNA into one of the pronuclei of ~100–300 recently fertilized mouse ova. Hogan, et al.., 1986, Manipulating the Mouse Embryo, Cold Spring Harbor Laboratory Press, Cold Spring Harbor, N.Y. Those eggs that survive injection were transferred to the oviducts of pseudopregnant mice (mated to vasectomized males). One to three weeks after birth a tail biopsy will be taken from the pups and genomic DNA analyzed by southern blot to determine the presence of the transgene. Mice that were positive for the presence of the transgene were mated to control mice to establish transgenic mouse lines. As a result of these experiments, two independent lines of transgenic mice that express the $\beta$-galactosidase under CTGF promoter control were produced. Both of these lines exhibit similar patterns of expression.

8.9 Chondrogenic Assay

Figure 7A:
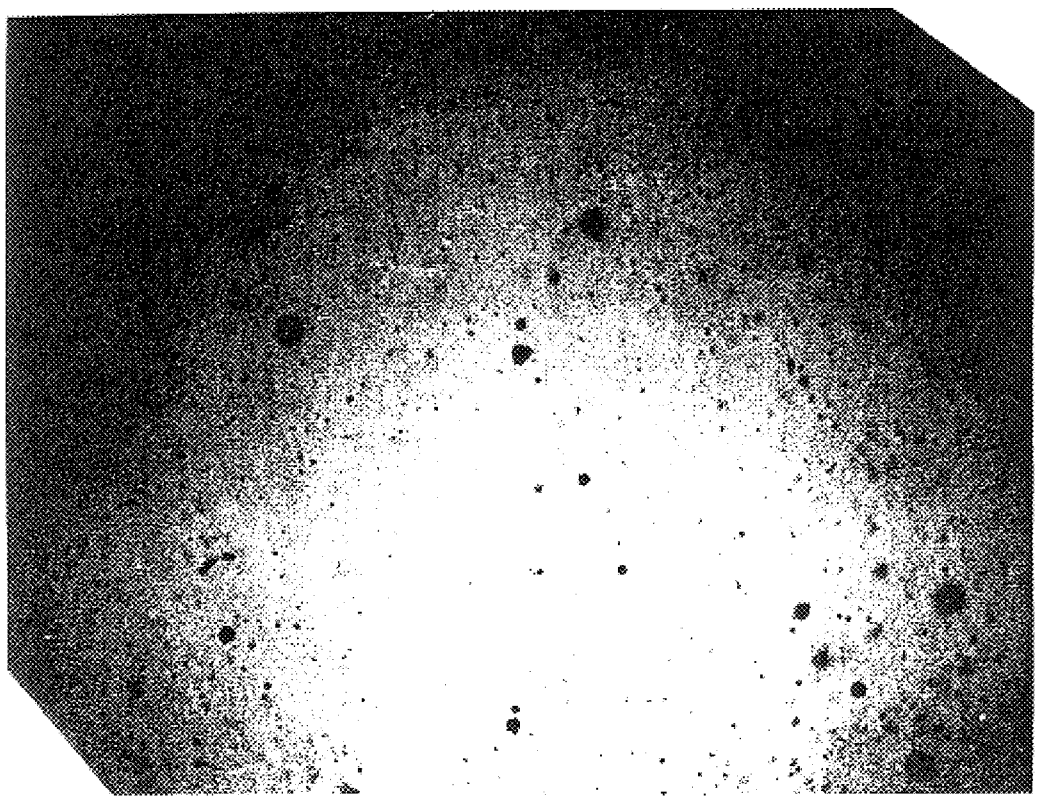
Figure 7B:
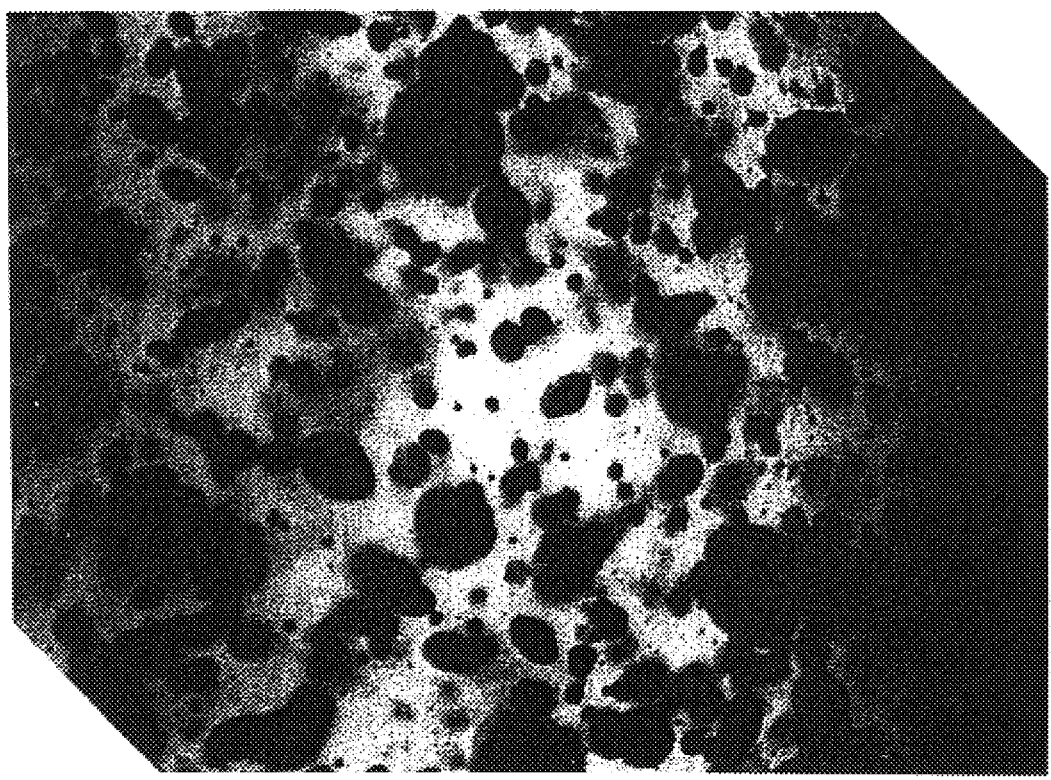
Figure 7C:
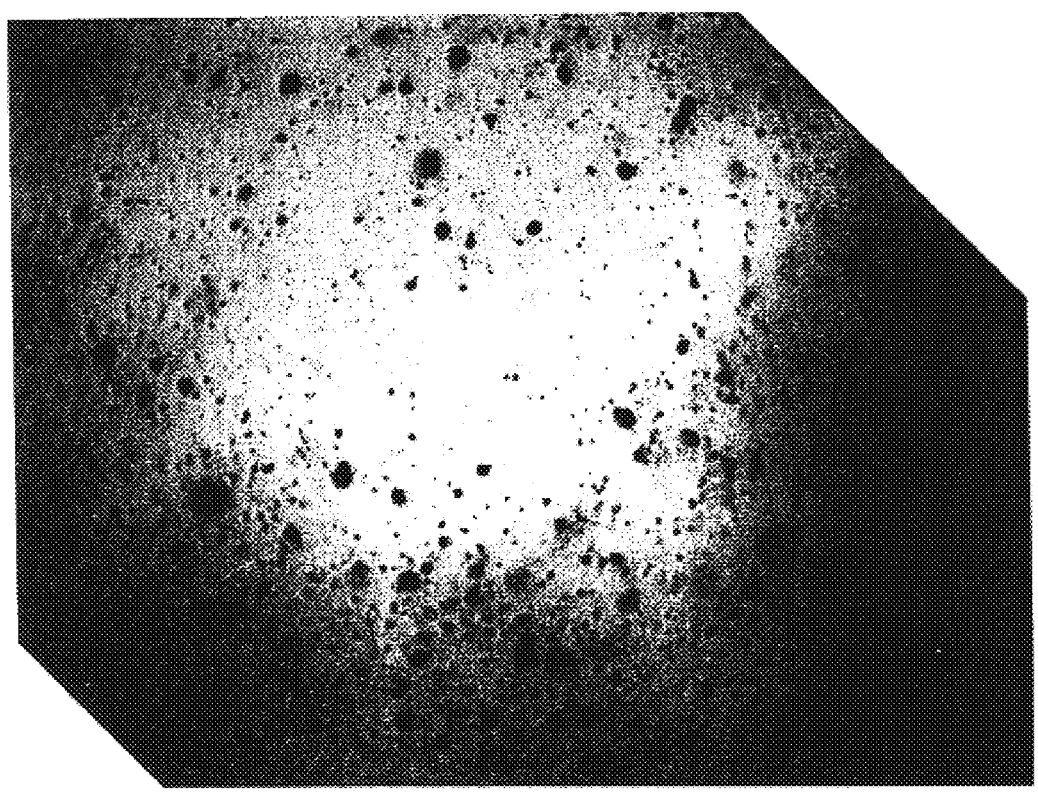
Figure 7D:
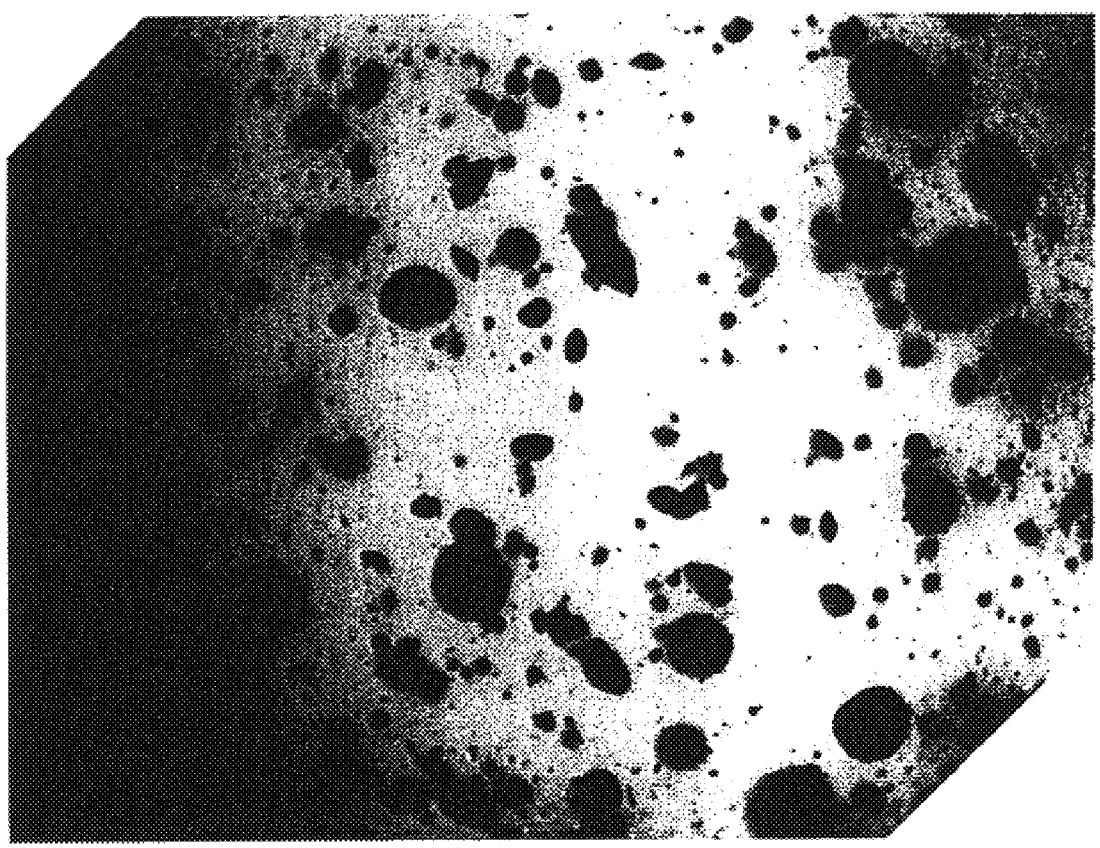

CTGF, as well as TGF-$\beta$ were tested in a chondrogenic assay as described in Seydin, et al., 1983, *J. Cell Biology* 97:1950–53. Briefly, primary cultures of embryonic muscle were obtained from cellular outgrowth of minced muscle tissue dissected from limbs of 19–20 day old Sprague-Dawley fetuses. For the chondrogenic assay, the cells were trypsinized and embedded in agarose, and overlayed with media containing no factors (FIG. 7A), TGF-$\beta$3 alone (FIG. 7B), TGF-$\beta$ and cholera toxin (FIG. 7C) or TGF-$\beta$, cholera toxin and CTGF (FIG. 7D). For each assay, media were changed every 2–3 days and after 21 days of culture stained with Toluidine blue as described in Horwitz and Dorfman, 1970, *J. Cell Biol.* 45:434–438.

As set forth in FIGS. 7A–7D, marked chondrocyte growth was observed where CTGF was added to media, indicating that CTGF stimulates chondrocyte growth, and the production of connective tissue matrix.

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited within the body of the instant specification are hereby incorporated by reference in their entirety.

Biological Deposits

The sequence of the CTGF of the invention was deposited with Genebank, Los Alamos National Laboratory, Los Alamos, N.Mex., 87545, *USA*, on Jul. 26, 1990, and given an accession no. M36965. The deposit of this CTFG sequence is for exemplary purposes only, and should not be taken as an admission by the Applicant that such deposit is necessary for enablement of the claimed subject matter.

In respect of all designated States in which such action is possible and to the extent that it is legally permissible under the law of the designated State, it is requested that a sample of the deposited micro-organism be made available only by the issue thereof to an independent expert, in accordance with the relevant patent legislation, e.g., EPC rule 28(4), United Kingdom Patent Rules 1982 rule 17(3), Australian Regulation 3.25(3) and generally similar provisions mutatis mutandis for any other designated State.

What is claimed is:

1. A method of inducing differentiation of mesenchymal stem cells, the method comprising contacting the mesenchymal stem cells ex vivo with an effective amount of Connective Tissue Growth Factor (CTGF) so as to induce differentiation thereof into a specific cell type selected from the group consisting of chondrocytes and osteoblasts.

2. The method of claim 1, further comprising contacting the mesenchymal stem cells with 5 azacytodine.

3. A method of inducing differentiation of mesenchymal stem cells into chondrocytes, the method comprising contacting the mesenchymal stem cell ex vivo with an effective amount of connective tissue growth factor.

4. A method of inducing differentiation of mesenchymal stem cells into osteoblasts, the method comprising contacting the mesenchymal stem cell ex vivo with an effective amount of connective tissue growth factor and 5-azacytodine.

* * * * *

SEQUENCE LISTING

<160> NUMBER OF SEQ ID NOS: 8

<210> SEQ ID NO 1
<211> LENGTH: 4214
<212> TYPE: DNA
<213> ORGANISM: Homo sapiens
<220> FEATURE:
<221> NAME/KEY: CDS
<222> LOCATION: (1025)...(1090)
<221> NAME/KEY: intron
<222> LOCATION: (1091)...(1204)
<221> NAME/KEY: CDS
<222> LOCATION: (1205)...(1426)
<221> NAME/KEY: intron
<222> LOCATION: (1427)...(1652)
<221> NAME/KEY: CDS
<222> LOCATION: (1653)...(1904)
<221> NAME/KEY: intron
<222> LOCATION: (1905)...(2033)
<221> NAME/KEY: CDS
<222> LOCATION: (2034)...(2246)
<221> NAME/KEY: intron
<222> LOCATION: (2247)...(2633)
<221> NAME/KEY: CDS
<222> LOCATION: (2634)...(2927)

<400> SEQUENCE: 1

```
tctagagctc gcgcgagctc taatacgact cactataggg cgtcgactcg atcccttttt      60
ctggaaacat tgatggccac tcgtcccttg tccttgccta tataaaactc ctacatatat     120
taagagaaaa ctaagcaaga gttttggaaa tctgccccag gagactgcat cctgagtcac     180
acgagtcttt gttctctttc ttgtcccaaa accgttacct caagtgacaa atgatcaaat     240
ctcaaatata gaattcaggg ttttacaggt aggcatcttg aggatttcaa atggttaaaa     300
gcaactcact ccttttctac tctttggaga gtttcaagag cctatagcct ctaaaacgca     360
aatcattgct aagggttggg gggagaaaac cttttcgaat tttttaggaa ttcctgctgt     420
ttgcctcttc agctacctac ttcctaaaaa ggatgtatgt cagtggacag aacagggcaa     480
acttattcga aaagaaata agaaataatt gccagtgtgt ttataaatga tatgaatcag     540
gagtggtgcg aagaggatag gaaaaaaaaa ttctatttgg tgctggaaat actgcgcttt     600
ttttttcctt tttttttttt tctgtgagct ggagtgtgcc agcttttca gacggaggaa     660 tgctgagtgt caagggggtca ggatcaatcc ggtgtgagtt gatgaggcag gaaggtgggg     720
aggaatgcga ggaatgtccc tgtttgtgta ggactccatt cagctcattg gcgagccgcg     780
gccgccggga gcgtataaaa gcctcgggcc gcccgcccca aactcacaca acaactcttc     840
cccgctgaga ggagacagcc agtgcgactc caccctccag ctcgacggca gccgccccgg     900
ccgacagccc cgagacgaca gcccggcgcg tcccggtccc cacctccgac caccgccagc     960
gctccaggcc ccgcgctccc cgctcgccgc caccgcgccc tccgctccgc ccgcagtgcc    1020 aacc atg acc gcc gcc agt atg ggc ccc gtc cgc gtc gcc ttc gtg gtc    1069
     Met Thr Ala Ala Ser Met Gly Pro Val Arg Val Ala Phe Val Val
       1               5                  10                  15 ctc ctc gcc ctc tgc agc cgg gtaagcgccg ggagccccg ctgcggccgg          1120
Leu Leu Ala Leu Cys Ser Arg
                20 cggctgccag ggagggactc ggggccggcc ggggagggcg tgcgcgccga ccgagcgccg    1180 ctgaccgccc tgtcctcccct gcag ccg gcc gtc ggc cag aac tgc agc ggg      1231
                             Pro Ala Val Gly Gln Asn Cys Ser Gly
                              25                  30
```

```
ccg tgc cgg tgc ccg gac gag ccg gcg ccg cgc tgc ccg gcg ggc gtg       1279
Pro Cys Arg Cys Pro Asp Glu Pro Ala Pro Arg Cys Pro Ala Gly Val
         35                  40                  45 agc ctc gtg ctg gac ggc tgc ggc tgc tgc cgc gtc tgc gcc aag cag       1327
Ser Leu Val Leu Asp Gly Cys Gly Cys Cys Arg Val Cys Ala Lys Gln
         50                  55                  60 ctg ggc gag ctg tgc acc gag cgc gac ccc tgc gac ccg cac aag ggc       1375
Leu Gly Glu Leu Cys Thr Glu Arg Asp Pro Cys Asp Pro His Lys Gly
 65                  70                  75 ctc ttc tgt gac ttc ggc tcc ccg gcc aac cgc aag atc ggc gtg tgc       1423
Leu Phe Cys Asp Phe Gly Ser Pro Ala Asn Arg Lys Ile Gly Val Cys
 80                  85                  90                  95 acc ggtaagaccc gcagccccca ccgctaggtg tccggccgcc tcctccctca            1476
Thr cgcccacccg cccgctggaa aagaaaccg ctcggactga gtttctttct ccagctgctg      1536
ccagcccgcc cctgcagcc cagatcccaa ctcgcatccc tgacgctctg gatgtgagag      1596
tgccccaatg cctgacctct gcatccccca ccctctctt ccttcctct tctcca gcc       1655
                                                            Ala aaa gat ggt gct ccc tgc atc ttc ggt ggt acg gtg tac cgc agc gga       1703
Lys Asp Gly Ala Pro Cys Ile Phe Gly Gly Thr Val Tyr Arg Ser Gly
         100                 105                 110 gag tcc ttc cag agc agc tgc aag tac cag tgc acg tgc ctg gac ggg       1751
Glu Ser Phe Gln Ser Ser Cys Lys Tyr Gln Cys Thr Cys Leu Asp Gly 115                 120                 125 gcg gtg ggc tgc atg ccc ctg tgc agc atg gac gtt cgt ctg ccc agc       1799
Ala Val Gly Cys Met Pro Leu Cys Ser Met Asp Val Arg Leu Pro Ser
130                 135                 140                 145 cct gac tgc ccc ttc ccg agg agg gtc aag ctg ccc ggg aaa tgc tgc       1847
Pro Asp Cys Pro Phe Pro Arg Arg Val Lys Leu Pro Gly Lys Cys Cys
                 150                 155                 160 gag gag tgg gtg tgt gac gag ccc aag gac caa acc gtg gtt ggg cct       1895
Glu Glu Trp Val Cys Asp Glu Pro Lys Asp Gln Thr Val Val Gly Pro
                 165                 170                 175 gcc ctc gcg ggtgagtcga gtcttcctct aagtcagggt cgtgattctc               1944
Ala Leu Ala
         180 tcccagggag ggagtcctaa ctgtgccgac cgaacgggga ataccttat caggcgtttt      2004 acatggtgtt tgtgtgctct gctctcgca gct tac cga ctg gaa gac acg ttt      2057
                                  Ala Tyr Arg Leu Glu Asp Thr Phe
                                                              185 ggc cca gac cca act atg att aga gcc aac tgc ctg gtc cag acc aca       2105
Gly Pro Asp Pro Thr Met Ile Arg Ala Asn Cys Leu Val Gln Thr Thr
         190                 195                 200 gag tgg agc gcc tgt tcc aag acc tgt ggg atg ggc atc tcc acc cgg       2153
Glu Trp Ser Ala Cys Ser Lys Thr Cys Gly Met Gly Ile Ser Thr Arg
205                 210                 215                 220 gtt acc aat gac aac gcc tcc tgc agg cta gag aag cag agc cgc ctg       2201
Val Thr Asn Asp Asn Ala Ser Cys Arg Leu Glu Lys Gln Ser Arg Leu
                 225                 230                 235 tgc atg gtc agg cct tgc gaa gct gac ctg gaa gag aac att aag           2246
Cys Met Val Arg Pro Cys Glu Ala Asp Leu Glu Glu Asn Ile Lys
             240                 245                 250 gtacatgttc tgctcctatt aactattttt cacaggaaaa acagtggata ggacccaact     2306
tagggctctt gcacgcttgt tagtataagc ccgttatctc caaaactatc taaccattga     2366
gctgttttgc tggaatgaga gcttgtgtaa tagcaaccac cagttttcca ctacgaaatc     2426
```

```
ttccacaggg ttagttaatt caagacattc caagagaggc tctggctatt tttggacata      2486
gcaaatgaga ctcaaacttc ctcccctcaa aatataaaca gaagtcagac aacagaagac      2546
taaaacacag agggttgaag aaagccactc ctcttgtaga gtcgctgatt ttttttttc       2606 ctctctcttt tcccttgtct tccttag aag ggc aaa aag tgc atc cgt act ccc     2660
                               Lys Gly Lys Lys Cys Ile Arg Thr Pro
                                               255                 260 aaa atc tcc aag cct atc aag ttt gag ctt tct ggc tgc acc agc atg       2708
Lys Ile Ser Lys Pro Ile Lys Phe Glu Leu Ser Gly Cys Thr Ser Met
            265                 270                 275 aag aca tac cga gct aaa ttc tgt gga gta tgt acc gac ggc cga tgc       2756
Lys Thr Tyr Arg Ala Lys Phe Cys Gly Val Cys Thr Asp Gly Arg Cys
        280                 285                 290 tgc acc ccc cac aga acc acc acc ctg ccg gtg gag ttc aag tgc cct       2804
Cys Thr Pro His Arg Thr Thr Thr Leu Pro Val Glu Phe Lys Cys Pro
    295                 300                 305 gac ggc gag gtc atg aag aag aac atg atg ttc atc aag acc tgt gcc       2852
Asp Gly Glu Val Met Lys Lys Asn Met Met Phe Ile Lys Thr Cys Ala
310                 315                 320 tgc cat tac aac tgt ccc gga gac aat gac atc ttt gaa tcg ctg tac       2900
Cys His Tyr Asn Cys Pro Gly Asp Asn Asp Ile Phe Glu Ser Leu Tyr
325                 330                 335                 340 tac agg aag atg tac gga gac atg gca tgaagccaga gagtgagaga              2947
Tyr Arg Lys Met Tyr Gly Asp Met Ala
                345 cattaactca ttagactgga acttgaactg attcacatct catttttccg taaaaatgat     3007 ttcagtagca caagttattt aaatctgttt ttctaactgg gggaaaagat tcccacccaa     3067 ttcaaaacat tgtgccatgt caaacaaata gtctatcttc cccagacact ggtttgaaga     3127 atgttaagac ttgacagtgg aactacatta gtacacagca ccagaatgta tattaaggtg     3187 tggctttagg agcagtggga gggtaccggc ccggttagta tcatcagatc gactcttata     3247 cgagtaatat gcctgctatt tgaagtgtaa ttgagaagga aaattttagc gtgctcactg     3307 acctgcctgt agccccagtg acagctagga tgtgcattct ccagccatca agagactgag     3367 tcaagttgtt ccttaagtca gaacagcaga ctcagctctg acattctgat tcgaatgaca     3427 ctgttcagga atcggaatcc tgtcgattag actggacagc ttgtggcaag tgaatttgcc     3487 tgtaacaagc cagatttttt aaaatttata ttgtaaatat tgtgtgtgtg tgtgtgtgtg     3547 tatatatata tatatatgta cagttatcta agttaattta agttgtttg tgccttttta      3607 ttttttgtttt taatgctttg atatttcaat gttagcctca atttctgaac accataggta    3667 gaatgtaaag cttgtctgat cgttgaaagc atgaaatgga tacttatatg gaaattctgc     3727 tcagatagaa tgacagtccg tcaaaacaga ttgtttgcaa aggggaggca tcagtgtctt     3787 ggcaggctga tttctaggta ggaaatgtgg tagctcacgt ttaatgaaca aatggcctta     3847 ttaaaaactg agtgactcta tatagctgat cagttttttca cctgaagcat ttgtttctac    3907 tttgatatga ctgttttttcg acagtttatt tgttgagagt gtgaccaaaa gttacatgtt    3967 tgcacctttc tagttgaaaa taagtgtat attttttttcta taagggctt ggttattcat     4027 ttatccttct aaacatttct gagttttctt gagcataaat aggaagttct tattaatcat     4087 aagataattc accaataatt ttctaaatat ctttaattat tctatacatt aataaattga     4147 ttattccata gaattttttat gtaaacatac ttcacactga atcaagtatc acagacttgc    4207 aggcata                                                                4214
```

<210> SEQ ID NO 2
<211> LENGTH: 22
<212> TYPE: PRT
<213> ORGANISM: Homo sapiens

<400> SEQUENCE: 2

Met Thr Ala Ala Ser Met Gly Pro Val Arg Val Ala Phe Val Val Leu
1               5                   10                  15

Leu Ala Leu Cys Ser Arg
            20

<210> SEQ ID NO 3
<211> LENGTH: 74
<212> TYPE: PRT
<213> ORGANISM: Homo sapiens

<400> SEQUENCE: 3

Pro Ala Val Gly Gln Asn Cys Ser Gly Pro Cys Arg Cys Pro Asp Glu
1               5                   10                  15

Pro Ala Pro Arg Cys Pro Ala Gly Val Ser Leu Val Leu Asp Gly Cys
            20                  25                  30

Gly Cys Cys Arg Val Cys Ala Lys Gln Leu Gly Glu Leu Cys Thr Glu
        35                  40                  45

Arg Asp Pro Cys Asp Pro His Lys Gly Leu Phe Cys Asp Phe Gly Ser
    50                  55                  60

Pro Ala Asn Arg Lys Ile Gly Val Cys Thr
65                  70

<210> SEQ ID NO 4
<211> LENGTH: 84
<212> TYPE: PRT
<213> ORGANISM: Homo sapiens

<400> SEQUENCE: 4

Ala Lys Asp Gly Ala Pro Cys Ile Phe Gly Gly Thr Val Tyr Arg Ser
1               5                   10                  15

Gly Glu Ser Phe Gln Ser Ser Cys Lys Tyr Gln Cys Thr Cys Leu Asp
            20                  25                  30

Gly Ala Val Gly Cys Met Pro Leu Cys Ser Met Asp Val Arg Leu Pro
        35                  40                  45

Ser Pro Asp Cys Pro Phe Pro Arg Arg Val Lys Leu Pro Gly Lys Cys
    50                  55                  60

Cys Glu Glu Trp Val Cys Asp Glu Pro Lys Asp Gln Thr Val Val Gly
65                  70                  75                  80

Pro Ala Leu Ala

<210> SEQ ID NO 5
<211> LENGTH: 71
<212> TYPE: PRT
<213> ORGANISM: Homo sapiens

<400> SEQUENCE: 5

Ala Tyr Arg Leu Glu Asp Thr Phe Gly Pro Asp Pro Thr Met Ile Arg
1               5                   10                  15

Ala Asn Cys Leu Val Gln Thr Thr Glu Trp Ser Ala Cys Ser Lys Thr
            20                  25                  30

Cys Gly Met Gly Ile Ser Thr Arg Val Thr Asn Asp Asn Ala Ser Cys
        35                  40                  45

```
Arg Leu Glu Lys Gln Ser Arg Leu Cys Met Val Arg Pro Cys Glu Ala
    50                  55                  60
Asp Leu Glu Glu Asn Ile Lys
65                  70
```

<210> SEQ ID NO 6
<211> LENGTH: 98
<212> TYPE: PRT
<213> ORGANISM: Homo sapiens

<400> SEQUENCE: 6

```
Lys Gly Lys Lys Cys Ile Arg Thr Pro Lys Ile Ser Lys Pro Ile Lys
1               5                   10                  15

Phe Glu Leu Ser Gly Cys Thr Ser Met Lys Thr Tyr Arg Ala Lys Phe
                20                  25                  30

Cys Gly Val Cys Thr Asp Gly Arg Cys Cys Thr Pro His Arg Thr Thr
            35                  40                  45

Thr Leu Pro Val Glu Phe Lys Cys Pro Asp Gly Glu Val Met Lys Lys
        50                  55                  60

Asn Met Met Phe Ile Lys Thr Cys Ala Cys His Tyr Asn Cys Pro Gly
65                  70                  75                  80

Asp Asn Asp Ile Phe Glu Ser Leu Tyr Tyr Arg Lys Met Tyr Gly Asp
                85                  90                  95

Met Ala
```

<210> SEQ ID NO 7
<211> LENGTH: 838
<212> TYPE: DNA
<213> ORGANISM: Mus musculus

<400> SEQUENCE: 7

```
tctttcttct cccactatat tccctgacac ttaggcttct gaagatagcc atttggtctg      60
aactcataaa cttattttc tagaaaacca tgcccagtca tacccctcgc ctgcctggac     120
cctgaagaca agttcttaca taagagtgc tgaaaatctt cctgggaacc tacatccttg     180
gctttcatat ctttcagcca tcaaatggc catctcagtg accaaagatc aatgcctgta     240
tttcagatac aaagttgca cataggaatt ctgggaggag aggaggcatt tcaaatggct     300
ataagcaccc ttctcctctc agtagaagaa caccaagaga ctacagcccc gtaaagaaaa     360
aaaaaaaaaa atccaaaaca aagaaaaaga aatattttt ttaatttcta ggggcccatg     420
gtatttgcct cttgagctat ttgagtcttg agaagttttt atgtcagtag ccagaactgg     480
caaagagatt tttaagaaga aaagatcaga gaaataatcg tttatttcta agttatattt     540
catcaggagg ggtgagaaga cgatatggag aaagttttac ttcttggtgt tgtgctggaa     600
acacagcgcc ttttttttt ttttcctggc gagctaaagt gtgccagctt tttcagacgg     660
aggaatgtgg agtgtcaagg ggtcaggatc aatccggtgt gagttgatga ggcaggaagg     720
tggggaggaa tgtgaggaat gtccctgttt gtgtaggact tcattcagtt ctttggcgag     780
ccggctcccg ggagcgtata aaagccagcg ccgcccgcct agtctcacac agctcttc      838
```

<210> SEQ ID NO 8
<211> LENGTH: 13
<212> TYPE: DNA
<213> ORGANISM: Artificial Sequence
<220> FEATURE:
<223> OTHER INFORMATION: TGF-beta responsive/regulatory element

<400> SEQUENCE: 8

-continued

| | |
|---|---|
| gtgtcaaggg gtc | 13 |